US012758620B2

(12) United States Patent
Shi et al.

(10) Patent No.: US 12,758,620 B2
(45) Date of Patent: Oct. 13, 2026

(54) PHARMACEUTICAL COMPOSITION CONTAINING INSULIN-LIKE GROWTH FACTOR-2 AND USE THEREOF

(71) Applicant: Shanghai Institute of Nutrition and Health, Chinese Academy of Sciences, Shanghai (CN)

(72) Inventors: Yufang Shi, Shuzhou (CN); Ying Wang, Shanghai (CN); Liming Du, Shanghai (CN); Liangyu Lin, Shanghai (CN)

(73) Assignee: Shanghai Institute of Nutrition and Health, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 18/300,286

(22) Filed: Apr. 13, 2023

(65) Prior Publication Data

US 2023/0364201 A1 Nov. 16, 2023

Related U.S. Application Data

(62) Division of application No. 16/464,902, filed as application No. PCT/CN2017/113341 on Nov. 28, 2017, now abandoned.

(30) Foreign Application Priority Data

Nov. 29, 2016 (CN) ........................ 201611073977.1

(51) Int. Cl.

| | |
|---|---|
| ***A61K 38/30*** | (2006.01) |
| ***A61K 40/17*** | (2025.01) |
| ***A61K 40/22*** | (2025.01) |
| ***A61K 40/24*** | (2025.01) |
| ***A61K 40/41*** | (2025.01) |
| ***A61P 5/50*** | (2006.01) |
| ***A61P 37/02*** | (2006.01) |
| ***C12N 5/0786*** | (2010.01) |

(52) U.S. Cl.

CPC .............. *A61K 38/30* (2013.01); *A61K 40/17* (2025.01); *A61K 40/22* (2025.01); *A61K 40/24* (2025.01); *A61K 40/416* (2025.01); *A61P 5/50* (2018.01); *A61P 37/02* (2018.01); *C12N 5/0645* (2013.01); *A61K 2239/38* (2023.05)

(58) Field of Classification Search

None

See application file for complete search history.

(56) References Cited

U.S. PATENT DOCUMENTS

| | | | |
|---|---|---|---|
| 2003/0027755 | A1 | 2/2003 | Guan et al. |
| 2004/0138116 | A1 | 7/2004 | Geenen |
| 2014/0255413 | A1 | 9/2014 | Adam et al. |
| 2019/0381147 | A1 | 12/2019 | Shi et al. |

FOREIGN PATENT DOCUMENTS

| | | | |
|---|---|---|---|
| CN | 1469752 | | 1/2004 |
| CN | 105007942 | | 10/2015 |
| WO | WO 93/25227 | A1 | 12/1993 |
| WO | WO 2004/019965 | A2 | 3/2004 |

OTHER PUBLICATIONS

Peng et al (MI, Article ID 8821610, 20 pages, 2023).*

Świdrowska-Jaros et al (PHMD, 70:743-750, 2016).*

Hourani et al (SR, 13:5202, 14 pages, 2023).*

Chaintreuil et al (FI, DOI 10.3389/fimmu.2023.1178337, pp. 1-9, 2023).*

Du et al (CM, 29, 1363-1375, 2019).*

Bhattacharya et al (RI, 39:769-780, 2019).*

International Search Report and Written Opinion for Application No. PCT/CN2017/113341, mailed Feb. 14, 2018. WIPO publication date: Jun. 7, 2018. Authorized Officer: Tingting Guo, State Intellectual Property Office of the P.R. China.

International Preliminary Report on Patentability for Application No. PCT/CN2017/113341, mailed Jun. 13, 2019.

Bergman et al., Insulin-like growth factor 2 in development and disease: a mini-review. Gerontology. 2013;59(3):240-9. doi: 10.1159/000343995. Epub Dec. 20, 2012.

Casellas et al., Insulin-like Growth Factor 2 Overexpression Induces α-Cell Dysfunction and Increases Beta-cell Susceptibility to Damage. J Biol Chem. Jul. 3, 2015;290(27):16772-85. doi: 10.1074/jbc.M115.642041. Epub May 13, 2015.

Chen et al., Regulation of PD-L1: a novel role of pro-survival signalling in cancer. Ann Oncol. Mar. 2016;27(3):409-16. doi:10.1093/annonc/mdv615. Epub Dec. 17, 2015.

Hamamura et al., IGF2-driven PI3 kinase and TGFbeta signaling pathways in chondrogenesis. Cell Biol Int. Oct. 2008;32(10):1238-46. doi:10.1016/j.cellbi.2008.07.007. Epub Jul. 16, 2008.

Holly et al., The Neglected Insulin: IGF-II, a Metabolic Regulator with Implications for Diabetes, Obesity, and Cancer. Cells. Oct. 6, 2019;8(10):1207. doi: 10.3390/cells8101207.

Horuk, Chemokine receptor antagonists: overcoming developmental hurdles. Nat Rev Drug Discov. Jan. 2009;8(1):23-33. doi: 10.1038/nrd2734. Epub Dec. 12, 2008.

Jiang et al., Macrophages: a double-edged sword in experimental autoimmune encephalomyelitis. Immunol Lett. Jul. 2014;160(1):17-22. doi: 10.1016/j.imlet.2014.03.006. Epub Mar. 31, 2014.

Kawanishi et al., Macrophage depletion by clodronate liposome attenuates muscle injury and inflammation following exhaustive exercise. Biochem Biophys Rep. Dec. 4, 2015;5:146-151. doi: 10.1016/j.bbrep.2015.11.022. eCollection Mar. 2016.

(Continued)

*Primary Examiner* — Brad Duffy

(74) *Attorney, Agent, or Firm* — Wolf, Greenfield & Sacks, P.C.

(57) ABSTRACT

Provided is the use of an insulin-like growth factor-2 for preparing a pharmaceutical composition, wherein the pharmaceutical composition is used for (i) promoting the expression of the macrophage PD-L1, and/or (ii) inhibiting the expression of the macrophage IL-β. Also provided is a pharmaceutical composition containing insulin-like growth factor-2 as an active ingredient.

6 Claims, 36 Drawing Sheets

Specification includes a Sequence Listing.

(56) References Cited

OTHER PUBLICATIONS

Kinne et al., Macrophages in rheumatoid arthritis. Arthritis Res. 2000;2(3):189-202. doi: 10.1186/ar86. Epub Apr. 12, 2000.

Lee et al., Pattern of the insulin-like growth factor II gene expression during early mouse embryogenesis. Development. Sep. 1990;110(1):151-9. doi: 10.1242/dev.110.1.151.

Mahida, The key role of macrophages in the immunopathogenesis of inflammatory bowel disease. Inflamm Bowel Dis. Feb. 2000;6(1):21-33. doi: 10.1097/00054725-200002000-00004.

Mercader et al., A Loss-of-Function Splice Acceptor Variant in IGF2 Is Protective for Type 2 Diabetes. Diabetes. Nov. 2017;66(11):2903-2914. doi: 10.2337/db17-0187. Epub Aug. 24, 2017.

Moreno et al., Therapeutic depletion of monocyte-derived cells protects from long-term axonal loss in experimental autoimmune encephalomyelitis. J Neuroimmunol. Jan. 15, 2016;290:36-46. doi: 10.1016/j.jneuroim.2015.11.004. Epub Nov. 10, 2015.

Shang et al., Role of regulatory T cells in pathogenic process of experimental allergic encephalomyelitis and multiple sclerosis. Chin J Neuromed. 2010, 9(07): 747-50. doi: 10.3760/cma.j.issn.1671-8925.2010.07.026.

Steinbach et al., The Role of Macrophages and Dendritic Cells in the Initiation of Inflammation in IBD. Inflamm Bowel Dis. Jan. 2014;20(1):166-75. doi: 10.1097/MIB.0b013e3182a69dca.

Uchimura et al., Insulin-Like Growth Factor II (IGF-II) Inhibits IL-1β-Induced Cartilage Matrix Loss and Promotes Cartilage Integrity in Experimental Osteoarthritis. J Cell Biochem. Dec. 2015;116(12):2858-69. doi: 10.1002/jcb.25232.

Yang et al., Insulin-like growth factor 2 enhances regulatory T-cell functions and suppresses food allergy in an experimental model. J Allergy Clin Immunol. Jun. 2014;133(6):1702-8.e5. doi: 10.1016/j.jaci.2014.02.019. Epub Apr. 1, 2014.

Yang et al., Progress in relationship between th17 and th1/treg cell. Imm J. Apr. 2010;26(4):353.

Zhou et al., Critical involvement of macrophage infiltration in the development of Sjögren's syndrome-associated dry eye. Am J Pathol. Sep. 2012;181(3):753-60. doi: 10.1016/j.ajpath.2012.05.014. Epub Jul. 4, 2012.

U.S. Appl. No. 16/464,902, filed Aug. 12, 2019, Shi et al.

PCT/CN2017/113341, Feb. 14, 2018, International Search Report and Written Opinion.

PCT/CN2017/113341, Jun. 13, 2019, International Preliminary Report on Patentability.

* cited by examiner

PHARMACEUTICAL COMPOSITION CONTAINING INSULIN-LIKE GROWTH FACTOR-2 AND USE THEREOF

RELATED APPLICATIONS

This application is a divisional of U.S. patent application Ser. No. 16/464,902, filed Aug. 12, 2019, which is a national stage filing under 35 U.S.C. § 371 of international application number PCT/CN2017/113341, filed Nov. 28, 2017, which claims the benefit of priority of Chinese application number CN 201611073977.1, filed Nov. 29, 2016, the entire contents of each of which are herein incorporated by reference.

REFERENCE TO AN ELECTRONIC SEQUENCE LISTING

The contents of the electronic sequence listing (X002570021US01-SEQ-KVC.xml; Size: 3,098 bytes; and Date of Creation: Apr. 13, 2023) is herein incorporated by reference in its entirety.

Field of the Invention

This invention relates to the field of biological medicine, and in particular to a pharmaceutical composition containing insulin-like growth factor-2 and use thereof.

Background

Macrophages are specialized immune cells distributed in all parts of the body. They remove the senescence cells, certain cells that cannot be recognized as their own, cell debris and so on through phagocytosis. As the professional antigen presenting cells, macrophages initiate the immune responses of unsensitized T cells and trigger the inflammatory response. However, inflammatory cytokines expressed by macrophages such as TNFα and IL-1 also play important roles in the pathogenesis of many autoimmune diseases. Removal of pathogenic macrophages has been shown to significantly inhibit autoimmune encephalomyelitis and inflammatory bowel diseases. In addition to their pro-inflammatory properties, macrophages can be regulated by different circumstances factors into cells with immunosuppressive effect, such as macrophages marked by expressing IL-10, Arginase I, etc, as well as macrophages with immunosuppressive function which are formed by different immune stimuli in the evolution process of monocytes to macrophages, thereby directly or indirectly regulating the body's immune response. It has been reported that spermidine treated macrophages are able to powerfully treat autoimmune diseases, indicating that macrophages with immunosuppressive effect have significant therapeutic effects in autoimmune diseases.

Currently, there is limited understanding on the application of macrophages to treat autoimmune diseases. New therapeutic strategies employing the plasticity of macrophages for autoimmune diseases are urgently need in the art.

Summary of the Invention

The present invention provides a composition containing insulin-like growth factor-2 and the uses thereof.

The first aspect of the invention provides a use of insulin-like growth factor-2 (IGF-2) to prepare a composition (including a chemical preparation and a pharmaceutical composition) to (i) increase PD-L1 expression in macrophage and/or (ii) inhibit IL-1β expression in macrophage.

In another preferred embodiment, the IGF-2 includes full length IGF-2 and an active fragment of IGF-2.

In another preferred embodiment, the active fragment of IGF-2 is an active fragment having amino acids from position 25 to position 91 of IGF-2.

In another preferred embodiment, the active fragment of IGF-2 is the amino acid sequence of position 25 to position 91 of IGF-2.

In another preferred embodiment, the IGF-2 is from human and non-human mammals.

In another preferred embodiment, the amino acid sequence of the IGF-2 is shown in SEQ ID NO: 1.

In another preferred embodiment, the pharmaceutical composition is also used for one or more of the purposes selected from the group consisting of:

(a) promoting oxidative phosphorylation metabolic pathway in macrophage;

(b) promoting differentiation of regulatory T cell;

(c) inhibiting differentiation of Th1 cell and/or Th17 cell; and (d) treating autoimmune disease.

In another preferred embodiment, the autoimmune disease is selected from the group consisting of multiple sclerosis, inflammatory bowel disease, autoimmune encephalomyelitis, autoimmune hepatitis, systemic lupus erythematosus, rheumatoid arthritis, insulin resistance, diabetes, liver cirrhosis or a combination thereof.

In another preferred embodiment, the insulin resistance or the diabetes is obesity-induced insulin resistance or obesity-induced diabetes.

In another preferred embodiment, the pharmaceutical composition comprises (a) IGF-2; and (b) a pharmaceutically acceptable carrier.

In another preferred embodiment, the pharmaceutical composition comprises 0.001-99 wt %, preferred 0.1-90 wt %, and more preferred 1-80% IGF-2, based on the total weight of the pharmaceutical composition.

In another preferred embodiment, the pharmaceutical composition comprises macrophage scavenger, and the scavenger is a formulation for removing macrophage or inhibiting macrophage migration.

In another preferred embodiment, the pharmaceutical composition comprises agonist of PD-L1.

In another preferred embodiment, the pharmaceutical composition is liquid or lyophilized formulation.

In another preferred embodiment, the pharmaceutical composition is an injection formulation.

The second aspect of the invention provides a use of macrophage treated with insulin-like growth factor-2 (IGF-2) for preparing a pharmaceutical composition for one or more of the purposes selected from the group consisting of:

(b) promoting differentiation of regulatory T cell;

(c) inhibiting differentiation of Th1 cell and/or Th17 cell; and (d) treating autoimmune disease.

In another preferred embodiment, macrophage is cultured in the presence of IGF-2 to obtain the macrophage treated with the IGF-2.

The third aspect of the invention provides a pharmaceutical composition comprising (a) IGF-2 or the active fragment thereof (such as active fragment having amino acids from position 25 to position 91), (b) optionally, macrophage scavenger, (c) optionally, PD-L1 promoter, and (d) a pharmaceutically acceptable carrier.

In another preferred embodiment, at least one of the components (b) and (c) is present.

In another preferred embodiment, the macrophage scavenger is an agent for removing macrophage or inhibiting macrophage migration.

In another preferred embodiment, the formulation of the pharmaceutical composition is an injection formulation, sustained release formulation or topical formulation.

In another preferred embodiment, the pharmaceutical composition is used for one or more of the purposes selected from the group consisting of:

(a) promoting PD-L1 expression in macrophage;
(b) inhibiting IL-1β expression in macrophage;
(c) promoting differentiation of regulatory T cell;
(d) inhibiting differentiation of Th1 cell and/or Th17 cell; and
(e) treating autoimmune disease.

In another preferred embodiment, the pharmaceutical composition comprises macrophage scavenger which depletes macrophage or suppresses macrophage migration.

In another preferred embodiment, the macrophage scavenger is selected from the group consisting of: CCR2 inhibitor (to inhibit macrophage migration), clodronate disodium liposome (to remove macrophage) and a combination thereof.

In another preferred embodiment, if the pharmaceutical composition comprises component (a), component (b) and component (c), the mass ratio of component (a): component (b):component (c) is (1-100):(1-100):(1-100).

In another preferred embodiment, if the pharmaceutical composition comprises component (a) and component (b), the mass ratio of component (a):component (b) is (1-100):(1-100).

In another preferred embodiment, if the pharmaceutical composition comprises component (a) and component (c), the mass ratio of component (a):component (c) is (1-100):(1-100).

In another preferred embodiment, the ratio (mg:mg) of IGF-2 active fragment having amino acids from position 25 to position 91 to macrophage scavenger ranges from 1:100 to 100:1, preferably, from 1:20 to 20:1.

In another preferred embodiment, the total content of IGF-2 active fragment having amino acids from position 25 to position 91 and macrophage scavenger is 1 to 99 wt % of the pharmaceutical composition, preferably, 5 to 90 wt % of the total pharmaceutical composition.

The fourth aspect of the invention provides a pharmaceutical composition comprising (a1) IGF-2 inhibitor, (b1) optionally, macrophage agonist, (c1) optionally, PD-L1 inhibitor, and (d1) a pharmaceutically acceptable carrier.

In another preferred embodiment, at least one of the components (b1) and (c1) is present.

In another preferred embodiment, the PD-L1 inhibitor includes PD-L1 antibodies.

In another preferred embodiment, if the pharmaceutical composition comprises component (a1), component (b1) and component (c1), the mass ratio of component (a1): component (b1):component (c1) is (1-100):(1-100):(1-100).

In another preferred embodiment, if the pharmaceutical composition comprises component (a1) and component (b1), the mass ratio of component (a1):component (b1) is (1-100):(1-100).

In another preferred embodiment, if the pharmaceutical composition comprises component (a1) and component (c1), the mass ratio of component (a1):component (c1) is (1-100):(1-100).

The fifth aspect of the invention provides a macrophage pre-treated with IGF-2.

In another preferred embodiment, in the macrophage, the PD-L1 expression is up-regulated and/or (ii) the IL-1β expression is down-regulated.

In another preferred embodiment, the up-regulation referred to that the ratio of PD-L1 expression quantity in treated macrophage (M1) to PD-L1 expression quantity in untreated macrophage (M0) M1/M0 is ≥1.5, preferably, M1/M0≥2.0, more preferably, M1/M0≥3.0. In another preferred embodiment, the down-regulation referred to that the ratio of IL-1β expression quantity in untreated macrophage (N0) to IL-1β expression quantity in treated macrophage (N1) N0/N1 is ≥1.5, preferably, N0/N1≥2.0, more preferably, N0/N1≥3.0.

In another preferred embodiment, the treatment includes exposing macrophage to IGF-2 or IGF-2 active fragment for a period of time (such as 0.1-24 hours).

The sixth aspect of the invention provides a pharmaceutical composition for regulating T cell differentiation, which comprises IGF-2 treated macrophage and a pharmaceutically acceptable carrier.

In another preferred embodiment, the regulating T cell differentiation referred to (b) promoting differentiation of regulatory T cell; and/or (c) inhibiting differentiation of Th1 and/or Th17 cell.

In another preferred embodiment, the pharmaceutical composition is used for treating autoimmune disease.

The seventh aspect of the invention provides a non-therapeutic method for (i) promoting PD-L1 expression and/or (ii) inhibiting IL-1β expression in macrophage, which comprises the following steps:

(a) culturing macrophage in the presence of IGF-2 to (i) enhance PD-L1 expression and/or (ii) inhibit IL-1β expression.

In another preferred embodiment, the concentration of IGF-2 is 1 ng/ml-100 μg/ml, preferably, 3 ng/ml-1 μg/ml, and more preferably, 5 ng/ml-50 ng/ml.

The eighth aspect of the invention provides a polypeptide with a sequence of position 25 to position 91 of SEQ ID NO: 1.

The ninth aspect of the invention provides a method for (i) enhancing PD-L1 expression and/or (ii) inhibiting IL-1β expression, which comprises the following steps:

(a) administrating IGF-2 to a subject in need.

In another preferred embodiment, the subject includes human and nonhuman mammal.

In another preferred embodiment, the dose of IGF-2 administered is 1 ng-1 mg/kg, preferably, 100 ng-100 μg/kg, and more preferably, 1-10 μg/kg.

In another preferred embodiment, the method further comprises the steps of:

(b) applying macrophage scavenger, which is an agent for removing macrophage or inhibiting macrophage migration, to a subject in need.

In another preferred embodiment, the dose and frequency of macrophage scavenger are administered in a conventional manner.

In another preferred embodiment, the administration includes administrating simultaneously or successively.

The tenth aspect of the invention provides a medicine kit, which contains:

(i) a first container, which contains an active ingredient (a) IGF-2 or a medicine containing the active ingredient (a);
(ii) a second container, which contains an active ingredients (b) macrophage scavenger or a medicine containing the active ingredient (b), wherein the macrophage scavenger is an agent for removing macrophage or inhibiting macrophage migration, and (iii) a specification describing the combined administration of the active ingredient (a) and the active ingredient (b) for treating an autoimmune disease.

In another preferred embodiment, the medicine in the first container or the second container is a formulation containing one single active ingredient (a) or a formulation containing one single active ingredient (b).

The eleventh aspect of the invention provides a use of the pharmaceutical composition in the third aspect and the medicine kit in the tenth aspect in preparation of a medicine for treating an autoimmune disease.

It should be understood that in the present invention, the technical features specifically described above and below (such as the Examples) can be combined with each other, thereby constituting a new or preferred technical solution, which needs not be described one by one, due to space limitations.

BRIEF DESCRIPTION OF DRAWINGS

FIG. 1A shows that IGF-2 can effectively alleviate the progress and degree of EAE.

FIG. 1B shows that IGF-2 can effectively inhibit mononuclear cell infiltration in the central nervous system.

FIG. 1C shows that IGF-2 can effectively inhibit MOG specific T cell proliferation in EAE mice.

FIGS. 1D-1G show that IGF-2 can effectively inhibit the cell proportion of Th1 and Th17 in EAE mice and promote the proportion of Treg.

FIG. 1H shows that IGF-2 does not directly effect the differentiation of Th1/Th17/Treg.

FIGS. 1I-1J show that IGF-2 promotes PD-L1 expression and inhibits IL-1β expression in the CD11b+F4/80+ macrophage in the spinal cord of EAE mice.

FIG. 2A shows that IGF-2 does not affect the number of macrophages in the spinal cord of EAE mice.

FIG. 2B shows that IGF-2 does not affect the number of macrophages in the spleen of EAE mice.

FIG. 2C shows that IGF-2 inhibits the expression level of IL-1β in CD11b+F4/80+ macrophages in the spleen of EAE mice.

FIG. 2D shows that IGF-2 promotes the expression level of PD-L1 in CD11b+F4/80+ macrophages in the spinal cord of EAE mice.

FIG. 2E shows that IGF-2 does not affect the expression levels of MHC-I, MHC-II, CD80, and CD86 in thioglycollate medium-induced peritoneal macrophages.

FIG. 2F shows that IGF-2 does not affect the expression levels of TNF-α, IL-6 and TGF-β in peritoneal macrophages under lipopolysaccharide (LPS) stimulation and thioglycollate medium-induction.

FIG. 2G shows that IGF-2 inhibits the mRNA levels of inducible nitric oxide synthase (iNOS) and the production of nitrite regulated by the enzyme, in the peritoneal macrophages under lipopolysaccharide (LPS) stimulation and thioglycollate medium-induction.

FIG. 3A shows that after IGF-2 pretreatment, under 100 ng/ml LPS stimulation, the ability of peritoneal macrophages induced by thioglycollate medium to express messenger RNA and precursor proteins of IL-1β is significantly decreased.

FIG. 3B shows that after IGF-2 pretreatment, under 100 ng/ml LPS stimulation, the IL-1β protein level secreted by peritoneal macrophages induced by thioglycollate medium is significantly decreased.

FIG. 3C shows that after IGF-2 pretreatment, under 100 ng/ml LPS stimulation, the PD-L1 protein level expressed by peritoneal macrophages induced by thioglycollate medium is significantly increased.

FIGS. 3D-3E show that IGF-2 treated macrophages are able to promote Treg differentiation depend on PD-L1.

FIG. 3F shows that IGF-2 treated macrophages significantly inhibits EAE.

FIG. 3G shows that IGF-2 treated macrophages can effectively promote the proportion of Tregs in EAE mice.

FIG. 4A shows that bone marrow derived macrophages treated with IGF-2 express significant higher level of PD-L1 under LPS stimulation.

FIGS. 4B-4C show that bone marrow derived macrophages treated with IGF-2 promote Treg through PD-L1.

FIG. 4D shows no change in the expression levels of MHC-I, MHC-II, CD80, and CD86 in bone marrow derived macrophages treated with IGF-2.

FIG. 5A shows that bone marrow derived macrophages treated with IGF-2 are effective in treating EAE.

FIGS. 5B-5C show that bone marrow derived macrophages treated with IGF-2 effectively increase the proportion of Treg in EAE mice.

FIG. 5D shows that bone marrow derived macrophages treated with IGF-2 relieved weight loss in IBD mice. Macrophages treated with IGF-2 shows the ability to effectively treat IBD.

FIG. 5E shows that bone marrow derived macrophages treated with IGF-2 can effectively prolong the survival time of mice with IBD.

FIGS. 5F-5G show that bone marrow derived macrophages treated with IGF-2 effectively increase the proportion of Treg cells in spleen in the IBD mice.

FIG. 6A shows that glucose consumption was significantly reduced in macrophages after IGF-2 treated.

FIG. 6B shows that lactic acid accumulation was significantly reduced in macrophages after IGF-2 treated.

FIG. 6C shows that NAD+/NADH ratio was significantly reduced in macrophages after IGF-2 treated.

FIG. 6D shows that the ability of oxidative phosphorylation and oxygen consumption was significantly increased in macrophages after IGF-2 treated.

FIG. 6E shows that extracellular acidification was significantly reduced in macrophages after IGF-2 treated.

FIG. 6F shows that macrophages preferred to conduct oxidative phosphorylation after IGF-2 treated.

FIG. 6G shows that oligomycin could inhibit the improvement of PD-L1 expression in peritoneal macrophages treated with IGF-2 and induced by thioglycollate medium.

FIG. 6H shows that oligomycin inhibits oxidative phosphorylation, and demonstrates that macrophages treated with IGF-2 have high expression of PD-L1 depended on aerobic respiration and the ability to promote the production of Treg.

FIG. 7A shows that IGF-2 protects IBD mice from body weight loss.

FIG. 7B shows that IBD mice received IGF-2 treatment have significant longer colon length.

FIG. 7C shows that numbers of mononuclear cells infiltration significantly decrease in colon after IGF-2 treatment.

FIGS. 7D-7E show that the proportion of Treg cells in the lamina propria of colon significantly increase in the IBD mice after IGF-2 treatment.

FIG. 7F shows that the expression of PD-L1 significantly increases in CD11b+F4/80+ macrophages in the lamina propria of colon of the IBD mice after IGF-2 treatment.

FIG. 7G shows that the expression level of IL-1β significantly decrease in CD11b+F4/80+ macrophages in the lamina propria of colon of the IBD mice after IGF-2 treatment.

FIG. 7H shows that IGF-2 treated macrophage relieves the body weight loss of experimental bowel disease mice.

FIG. 7I shows that IGF-2 treated macrophage effectively prolongs the survival time of the IBD mice.

FIG. 7J shows that the proportion of Treg cells in spleen significantly increase in the IBD mice injected with IGF-2 treated macrophage.

FIGS. 8A-8B show that IGF-2 significantly up regulates the proportion of Tregs in the peritoneal lymph nodes of mice with IBD.

FIG. 8C shows that IGF-2 does not affect the proportion of spleen macrophages in mice with IBD.

FIG. 8D shows that IGF-2 upregulates the proportion of CD11b+F4/80+ macrophages in the colon lamina propria of mice with IBD.

FIG. 8E shows that IGF-2 significantly downregulates the expression level of IL-1β in spleen macrophages in mice with IBD.

FIG. 8F shows that IGF-2 significantly up regulates the expression level of PD-L1 in spleen macrophages in mice with IBD.

FIG. 9A shows that IGF-2 treated macrophages can significantly increase the proportion of Tregs in peritoneal lymph nodes of IBD mice.

FIG. 9B shows that IGF-2 pre-treated macrophages can significantly increase the proportion of Tregs in lamina propria of colon of IBD mice.

IGF-2 applied in the reference and description of FIGS. 1A-13B is an active fragment of IGF-2 containing amino acids from position 25 to position 91. ($IGF_{25-91}$)

DETAILED DESCRIPTION OF THE INVENTION

After extensive and thorough studies, the inventors have firstly established a pharmaceutical composition containing insulin-like growth factor-2 and use thereof. This invention provides the use of IGF-2 and its active fragment for preparing a pharmaceutical composition. The pharmaceutical composition can be used for (i) enhancing PD-L1 expression and/or (ii) inhibiting IL-1β expression in macrophages. The invention also provides a pharmaceutical composition containing insulin-like growth factor-2 as an active ingredient.

Specifically, in the invention, it is found that both insulin-like growth factor-2 (IGF-2) and the active fragment having amino acids from position 25 to position 91 of IGF-2 ($IGF_{25-91}$) show significant therapeutic effects in the treatment of animal models of multiple sclerosis and colitis (experimental autoimmune encephalomyelitis and DSS-induced inflammatory bowel diseases), and can significantly inhibit the progression of the disease and the tissue damage and inflammatory infiltration in corresponding site. More importantly, $IGF_{25-91}$ indirectly upregulates regulatory T cells (Treg) by inducing macrophages with low IL-1 expression and high PD-L1 expression, thereby promoting the recovery of autoimmune diseases. $IGF_{25-91}$ mainly promotes the reprogramming of macrophages into macrophages with immunosuppressive function by affecting the aerobic glycolysis and oxidative phosphorylation pathways of macrophages, and such macrophages treated with $IGF_{25-91}$ have a very significant effect on the treatment of autoimmune diseases. Based on the therapeutic effect of $IGF_{25-91}$ on autoimmune diseases, the present invention clarifies the regulatory mechanism of $IGF_{25-91}$ on macrophages, and it is found that $IGF_{25-91}$ induces the application potential of macrophages with immunosuppressive function in the treatment of autoimmune diseases, thus forming a new technique for macrophage immunotherapy.

Insulin-Like Growth Factor-2

Figure 11:
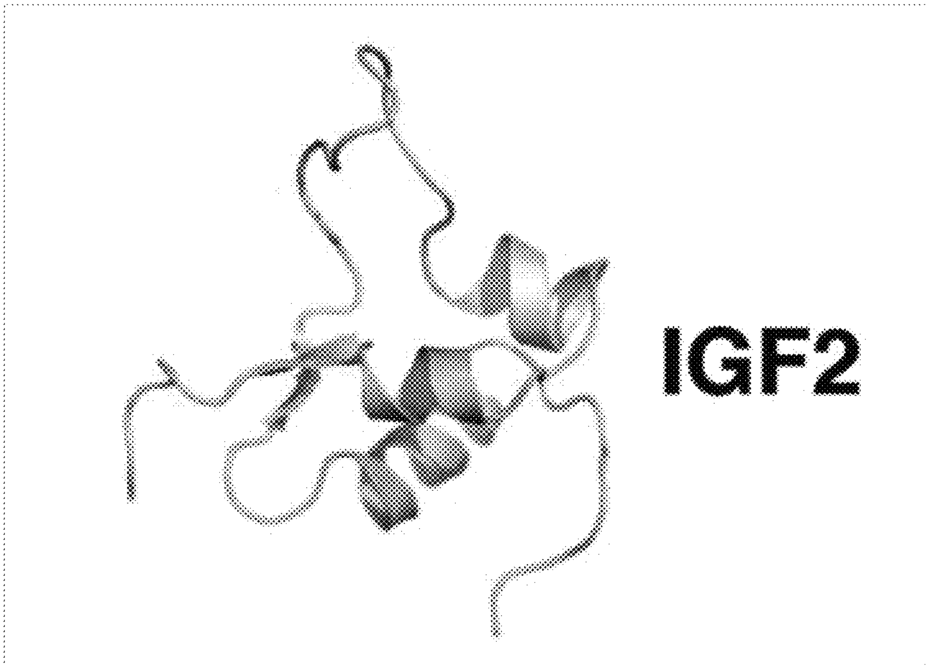
FIG. 11 shows the tertiary structure of insulin-like growth factor-2 (IGF-2).
Figure 12:
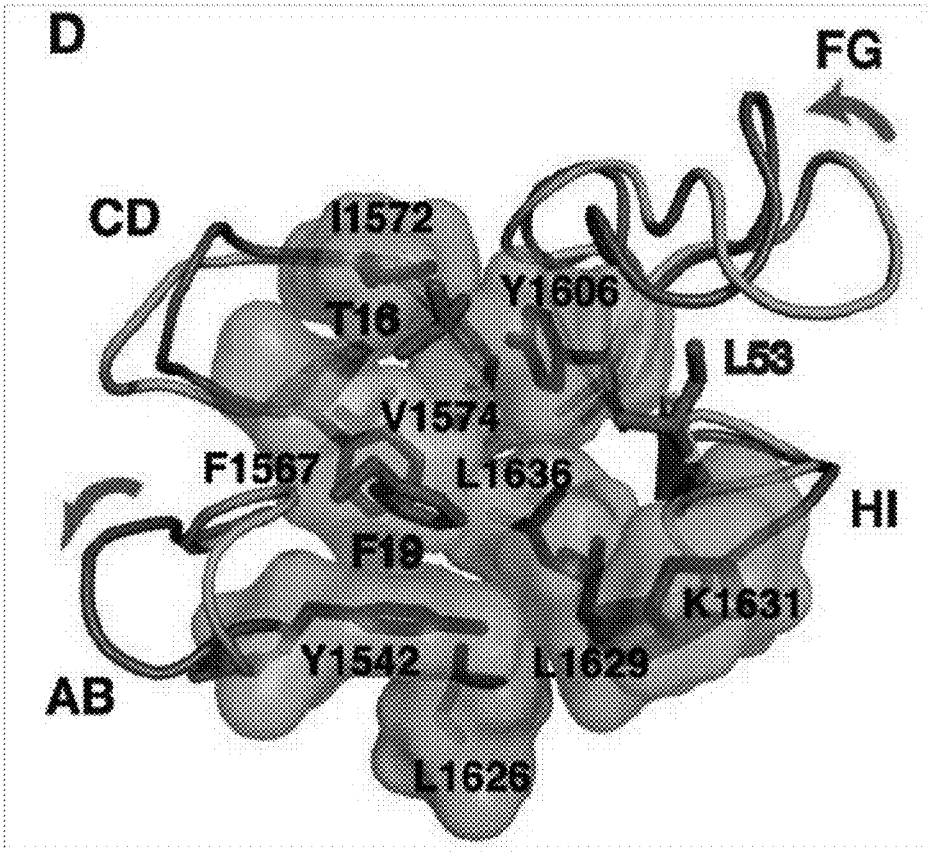
FIG. 12 shows the key binding sites of insulin-like growth factor-2 (IGF-2) to the receptor.

Insulin-like growth factor-2 (IGF-2) is a growth factor mainly synthesized in the liver and is abundantly present in the blood. IGF-2 has anti-apoptosis, growth regulation, insulin-like and mitotic functions. IGF-2 precursor protein, which is translated from mRNA, consists of 180 amino acids, as shown in the sequence: MGIPMGKSMLVLLT-FLAFASCCIAAYRPSETLCG-GELVDTLQFVCGDRGFYFSRPASRV SRRSR-GIVEECCFRSCDLALLETYCATPAKSERDVSTPPTVL PDNFPRYPVGKFFQYDT WKQSTQRLRRGLPALL-RARRGHVLAKELEAFREAKRHRPLIALPTQDPAHG-GAPPEMA SNRK (SEQ ID NO: 1); The active form produced after modification after translation consists of 67 amino acids, as shown in the sequence: AYRPSETLCG-GELVDTLQFVCGDRGFYFSRPASRVSRRSR-GIVEECCFRSCDLALLETY CATPAKSE (SEQ ID NO: 2). The tertiary structure of IGF-2 is composed of three α-helixes and two β-sheets as shown in FIG. 11, wherein amino acids 11G-21C forms a helix, 25G-27Y forms the first sheet, the second helix is 42I-49R, the third helix is 53L-58T and the second sheet is 59Y-61A. It is predicted that T16 and F19 on the first helix and L63 on the third helix are sites where IGF-2 binds to receptor of IGF-2 as shown in FIG. 12.

At present, it is generally believed that IGF-2 has an important role in embryo development and can promote embryo development and organ formation. It has also been reported to be linked to memory and reproduction, and studies in genetically deficient mice have shown that lack of insulin-like growth factor-2 signaling can lead to poor brain development.

The present invention has found that administration of IGF-2 or active fragment having the amino acids sequence from position 25 to position 91 of IGF-2 ($IGF_{25-91}$) alone can effectively treat experimental autoimmune encephalomyelitis or inflammatory bowel disease, which are two autoimmune diseases. In the lesion site, such as the spinal cord or colon of the diseased mice, the proportion of regulatory T cells in the $IGF_{25-91}$ treatment group was significantly increased, and the proportions of TH1 and TH17 cells were significantly decreased.

However, when the in vitro T cell differentiation system was used to verify the effect of $IGF_{25-91}$ on T cell differentiation, it was found that $IGF_{25-91}$ could not directly affect the efficiency of T cell differentiation into Th1, Th17 and Treg. These studies suggest that $IGF_{25-91}$ has an indirect effect on the proportion change of T cell subsets. Significant changes in the macrophage phenotype were also observed when insulin-like growth factor-2 was used to treat autoimmune diseases. It was found in the study that the expression of IL-1β in macrophages at the injury site of mice treated with $IGF_{25-91}$ was significantly decreased, while the expression of PD-L1 was significantly increased, suggesting that $IGF_{25-91}$ played a role in inhibiting autoimmune diseases through promoting the proportion of macrophages with anti-inflammatory effects.

It is found in the study that $IGF_{25-91}$ does not directly induce the expression of anti-inflammatory genes in macrophages. However, the bone marrow or enterocoelia derived mature macrophages treated with $IGFIGF_{25-91}$ exhibit significantly decrease of IL-1β expression and significantly increase of PD-L1 expression in response to lipopolysaccharide stimulation. Macrophages play an important role in the occurrence and development of autoimmune diseases. A series of studies have shown that macrophages can exert strong proinflammatory ability under the stimulation of inflammatory factors such as interferon and lipopolysaccharide, which aggravate the process of autoimmune diseases. Studies have shown that insulin-like growth factor-2 alters the response of macrophages to inflammatory factors, and macrophages overexpress the anti-inflammatory molecule PD-L1 under the condition of proinflammatory stimulation. Therefore, the treatment of autoimmune diseases by $IGF_{25-91}$ is likely to be achieved by reprogramming macrophages.

In order to clarify the role of macrophages treated with $IGF_{25-91}$ in regulating Treg, macrophages induced by $IGF_{25-91}$ were co-cultured with T cells after LPS pre-stimulation. It was found that macrophages treated with $IGF_{25-91}$ could significantly promote the differentiation of Treg, and the promotion depended on the high expression of PD-L1. Further, the studies showed that macrophages treated with $IGF_{25-91}$ could also be directly used to treat autoreactive encephalomyelitis and inflammatory bowel disease. During the treatment process, the infusion of these macrophages also promoted the increase of Treg proportion in mice.

In order to further explain how $IGF_{25-91}$ affects the expression of PD-L1 in macrophages, a detailed comparison was made between macrophages treated with $IGF_{25-91}$ and control cells. It was found that macrophages treated with $IGF_{25-91}$ can significantly change the status of glucose metabolism pathway of macrophages, making them more apt to oxidative phosphorylation metabolic pathway. When blocking macrophages mitochondrial oxidative phosphorylation, the high expression of PD-L1 and the ability to promote Treg differentiation induced by insulin-like growth factor-2 in macrophages also disappeared. These studies illustrate that $IGF_{25-91}$ endows macrophages with the ability of promoting Treg generation and treating autoimmune diseases by changing the metabolism tendencies of macrophages.

In conclusion, $IGF_{25-91}$ plays a therapeutic role in multiple sclerosis and inflammatory bowel disease by inducing immunosuppressive macrophages and up-regulating regulatory T cells. Macrophages treated with $IGF_{25-91}$ may play a therapeutic role in autoimmune diseases. In addition, the targeted regulation of aerobic glycolysis and oxidative phosphorylation in macrophages can induce the production of immunosuppressant macrophages and play a role in the treatment of various autoimmune diseases.

Pharmaceutical Composition and Instructions

This invention provides a pharmaceutical composition for (i) promoting PD-L1 expression and/or (ii) inhibiting IL-1β expression in macrophages. It contains a safe and effective dose of IGF-2 (or its active fragments) or contains IGF-2 treated macrophages.

The pharmaceutical composition of the invention can be used for (i) promoting PD-L1 expression and/or (ii) inhibiting IL-1β expression in macrophages. The pharmaceutical composition can be used together with other autoimmune diseases therapies.

The pharmaceutical composition of the invention can also contain macrophage scavenger which is an agent for removing macrophages or inhibiting macrophage migration. Experiments showed that the combination therapy of $IGF\text{-}2_{25-91}$ and macrophage scavenger played a more optimized role in the treatment of inflammatory diseases by reprogramming macrophages with immunosuppressive function.

The invention also provides a medicine kit comprising:

(i) a first container which contains an active ingredient (a) IGF-2 or a medicine containing the active ingredient (a);

(ii) a second container which contains an active ingredients (b) macrophage scavenger or a medicine containing the active ingredient (b), wherein the macrophage scavenger is agent for removing macrophage or inhibiting macrophage migration, and (iii) an specification describing a combined administration of the active ingredient (a) and the active ingredient (b) for treating autoimmune diseases.

The pharmaceutical composition of the invention contains a safe and effective dose of IGF-2 and a pharmaceutically acceptable carrier. The carrier includes (not limited to): saline, buffer solution, glucose, water, glycerin, alcohol, powder and the combination thereof. The formulation of the medicine should be compatible with the method of administration.

The pharmaceutical composition of the invention can be prepared in the form of an injection, for example, by a conventional method using saline or an aqueous solution containing glucose and other adjuvants. Pharmaceutical compositions such as tablets and capsules may be prepared by conventional methods. Pharmaceutical composition such as injection, solution, tablet and capsule should be manufactured under sterile conditions. The pharmaceutical composition of the invention can also be made into powder for atomizing inhalation. The dose of the active ingredient is an effective dose, such as about 1 μg/kg-50 mg/kg, about 5 μg/kg-10 mg/kg, about 10 μg/kg-5 mg/kg of body weight per day. The pharmaceutical composition can be administered together with other therapies.

The pharmaceutical composition of the invention can be administered to a subject (such as human and non-human mammal) in routine manner. The representative way for administration includes (but not limit to): oral administration, injection and aerosol inhalation.

The pharmaceutical composition should be administered to a mammal in a safe and effective dose. The safe and effective dose is usually at least 10 μg/kg of body weight and no more than 50 mg/kg of body weight under most conditions. The preferred dose should range from 10 μg/kg to 20 mg/kg of body weight. The exact dose should be determined according to the administration route and the patient health conditions which are all within the expertise of a skilled physician.

The main advantages of the present invention includes:

(a) IGF-2 and the active fragment thereof (from position 25 to position 91) can (i) promote PD-L1 expression and/or (ii) inhibit IL-1β expression in macrophages.

(b) Macrophages treated with IGF-2 or the active fragment thereof can promote Treg differentiation and inhibit Th1 cell and/or Th17 cell differentiation so as to treat autoimmune diseases.

(c) Combination therapy of IGF-2 or active fragment thereof with macrophage scavenger can be used for treating autoimmune diseases.

The present invention will be further illustrated below with reference to the specific examples. It should be understood that these examples are only to illustrate the invention but not to limit the scope of the invention. For the experimental methods in the following examples the specific conditions of which are not specifically indicated, they are performed under routine conditions, or as instructed by the manufacturers, unless otherwise specified. Unless indicated otherwise, parts and percentage are weight parts and weight percentage.

Materials and Methods

Establishment and Treatment of Experimental Autoreactive Encephalomyelitis EAE Model (1) Preparation Before Experiment Preparation of complete freund's adjuvant: heat inactivated Mycobacterium tuberculosis (purchased from sigma) was added into incomplete freund's adjuvant until the final concentration reached 5 mg/ml, and the solution were thoroughly mixed before use.

Emulsification of antigen: Two glass syringes were connected through a three-way tube, an equal volume of antigen solution (300 μg MOG in 100 μL PBS) and 100 μL of complete Freund's adjuvant were added into the syringes, and the bubbles in the syringes were removed and the syringes were pushed back and forth to obtain an emulsion. After about 500 pushes, the push resistance would gradually increase indicating the ingredients were fully mixed into an emulsified state.

Preparation of pertussis toxin (PT) solution: pertussis toxin was dissolve in PBS at a working concentration of 1 ng/μL and 200 μL per mouse was injected through the tail vein.

(2) Establishment and Treatment of EAE Model

On day 0, 200 μL of the emulsified antigen was subcutaneously injected into the back of C57BL/6 mice (purchased from the Slack Shanghai Laboratory Animal Center of the Chinese Academy of Sciences) for antigen immunization, and 100 μL was injected into each side of the chest corresponding to the back. Meanwhile, 200 μL/mouse of PT was injected through the tail vein.

On day 2, 200 μL/mouse of PT was injected again through the tail vein.

From the ninth day, insulin-like growth factor 2 was used for treatment via intraperitoneal injection at a dose of 5 ng/mouse everyday. The saline treated group served as a positive control.

When macrophages were used for treatment, $5\times10^6$ macrophages were injected intraperitoneally on Day 9, 11, and 13, respectively, and clinical scores were recorded daily.

(3) Clinical Scoring of EAE

0: clinically normal; 0.5: tail drooping at the tip; 1: whole tail paralysis; 2: hind legs weakness; 3: one hind limb paralysis; 4. both hind limbs paralysis; 5: died.

2. Extraction of Lymphocytes from Spinal Cord

The spinal cord was removed from EAE mice and washed with PBS. The spinal cord was mechanically ground on a 70 μm pore size cell screen to obtain a single cell suspension. The obtained cell suspension was centrifuged, and the cells were resuspended in 30% percoll, and an equal volume of 70% percoll solution was gently added to the bottom. Centrifugation was carried out at 2000 rpm for 20 minutes at room temperature under zero acceleration. After centrifugation, cells were aspirated from the liquid junction layer of high-low density and washed twice with PBS to obtain lymphocytes.

3. In Vitro Proliferation Experiment of Splenocytes

After the EAE mice were sacrificed, the spleen of the mice was removed and a single cell suspension was obtained. The splenocytes were plated in a U-bottom 96-well plate at a number of $3\text{-}5\times10^5$ per well, and MOG was added to 20 μg/ml.

After incubation at 37° C. for 72 hours in an incubator, H3 labeled thymidine was added. After 6 hours, the well plate was freeze-thawed repeatedly and then vacuum-adsorbed onto a special filter. The scintillation solution was added and then detected on the machine.

4. Establishment and Treatment of Inflammatory Bowel Disease IBD Model

Dextran sodium sulfate (DSS) was formulated into a solution at a mass to volume ratio of 2.5:100, filtered with a 22 μm strainer to ensure sterility, and sealed with a parafilm.

8-10 weeks aged C57/BL6 female mice (purchased from Slack Shanghai Laboratory Animal Center of the Chinese Academy of Sciences) were selected and used. Dextran sodium sulfate solution was used to replace the drinking water to induce the model. The mice weight and feces were observed every day. The dextran sulfate sodium solution was changed or added every other day.

From the day of model induction, insulin-like growth factor-2 was injected intraperitoneally at a dose of 50 ng/mouse everyday. The saline treated group served as a positive control.

When macrophages were used for treatment, $5\times10^7$ macrophages were injected intraperitoneally on Day 1, 3, and 5, respectively, and the change of body weight was recorded daily.

5. Extraction of Lymphocyte from Colon Tissue

The colon was removed from the IBD mice, the feces were removed and washed with PBS. Then the colon was cut into 2 cm sections and rinsed twice in HBSS (1 mM DTT and 5 mM EDTA) under conditions of 250 rpm for 20 min at 37° C. The washed colon tissue was cut as much as possible with scissors and added into HBSS containing DNAase I, dispase and type VIII collegenase under the conditions of 250 rpm for 30 min at 37° C. The obtained cell suspension was centrifuged, and the cells were resuspended in 40% percoll, and an equal volume of 80% percoll solution was gently added to the bottom. Centrifugation was carried out at 2000 rpm for 20 minutes at room temperature under zero acceleration. After centrifugation, cells were aspirated from the liquid junction layer of high-low density and washed twice with PBS to obtain lymphocytes.

6. Hippocampal Test

Cells were implanted on the hippocampal test plate at a density of $1\times10^5$ cells per well. XF culture was supplemented with 10 mM glucose, 2 mM glutamine and 2 mM pyruvate to prepare a test medium. The cells were washed twice with the test medium before testing on the machine. Metabolic inhibitors were prepared using test medium: 1 μM oligomycin, 0.75 μM FCCP, 100 μM rotenone and 1 μM Mantimycin. The consumption rate of oxygen and the concentration of extracellular hydrogen ion at basic status and under drug stimulation conditions were measured. The instrument used was Extracellular flux analyzer.

7. Preparation and Treatment of Macrophages

The preparation process of bone marrow derived macrophages was as follows: mouse bone marrow was blown out with 1 ml syringe. After being full dispersed, the cells were centrifuged according to the condition of 400 g for 5 min. The supernatant was discarded, the cells were blown into single cell suspension, and the cells were laid on an uncoated culture dish in DMEM/F12 completely medium (containing 10% FBS, 20% L929 supernatant, 100 U/ml Penicillin, 100 U/ml Streptomycin, 2 mm L-Glutamine). At the fourth day of culture, 5 ml solution was added, and the cells were further cultured for 6 days, and mature macrophages could be obtained. IGF-2 stimulation was added on Day 1, 3 and 5, respectively.

The preparation process of peritoneal derived macrophages was as follows: 2 ml of 4% thioglycollate solution was intraperitoneally injected into 8-12 weeks aged C57BL/6 mice, cytokines or PBS were intraperitoneally injected daily every day. On the third day, mice were sacrificed. Macrophages in abdominal cavity were blown out by using a 10 ml syringe with 10 ml volume of PBS. After centrifugation, the cells were scattered to form a single cell suspension, and were then inoculated in an uncoated cell dish or a 6-well plate, for following experiments.

8. Co-Culture System of Macrophages and Naïve T Cells

Macrophages derived from mature bone marrow or peritoneal were stimulated with LPS for 24 hours. The stimulation solution was aspirated and cells were washed with PBS for three times to fully remove the residual LPS. Then, the macrophages ($2.5\times10^5$) and selected $CD4^+CD62L^+$ T cells ($1\times10^6$) were laid on a 96-well plate. After 72 hours of co-culture, the cells were blown out for flow cytometry staining and analysis.

9. Establish Obesity Modeling by High-Fat Diet Induction

C57/BL6 mice (purchased from slake Shanghai experimental animal center of Chinese academy of sciences) were fed with a high-fat diet for 20 weeks, starting from the 5th week.

10. Glucose Tolerance Test

The mice were starved overnight, and 1 g glucose/kg body weight was intraperitoneally injected. At different time points, a drop of tail venous blood of each mouse was siphoned into the blood glucose test paper, and blood glucose was measured with a blood glucose meter.

11. Insulin Tolerance Test

The mice were starved overnight for about 16 hours, and 0.75 U insulin/kg body weight was intraperitoneally injected. At different time points, a drop of tail venous blood of each mouse was siphoned into the blood glucose test paper, and blood glucose was measured with a blood glucose meter, and accurate timing was conducted with a timer.

Example 1

Figure 1A:
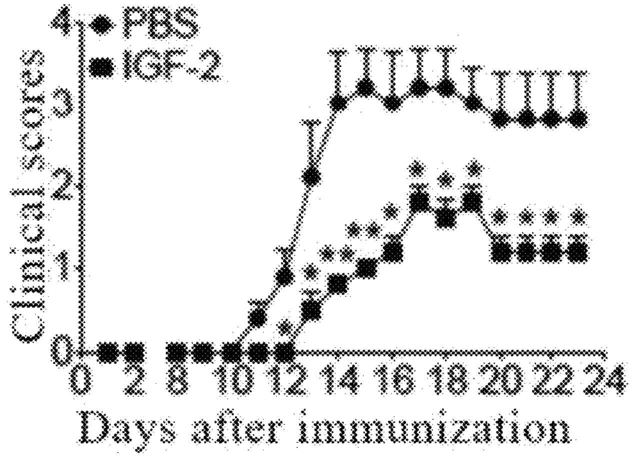
FIGS. 1A-1J show that insulin-like growth factor 2 (IGF-2) is effective in treating EAE.
Figure 1B:
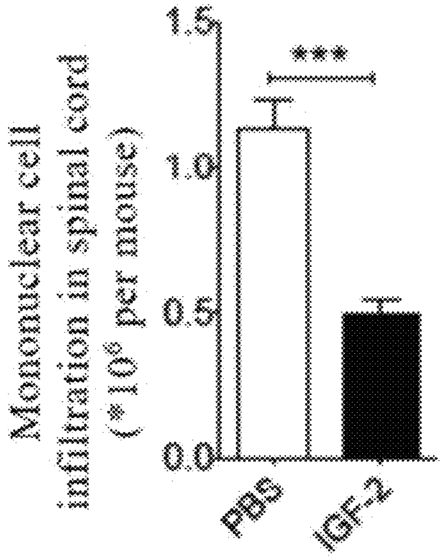
Figure 1C:
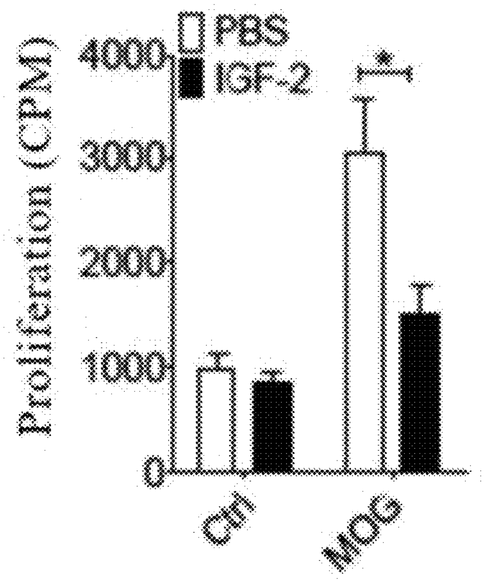
Figure 1D:
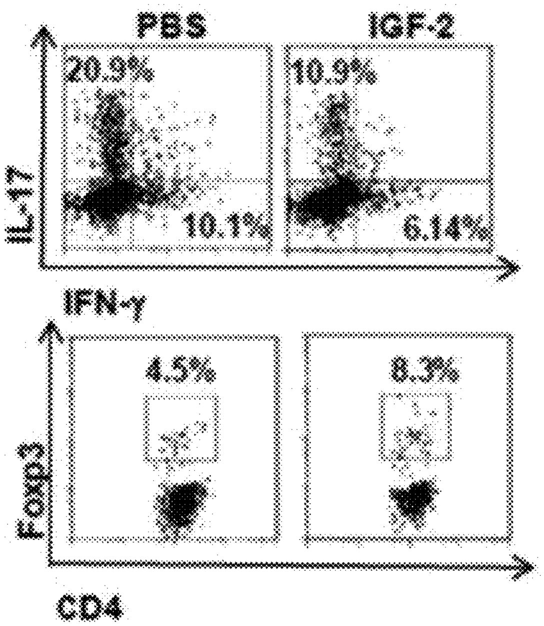
Figure 1E:
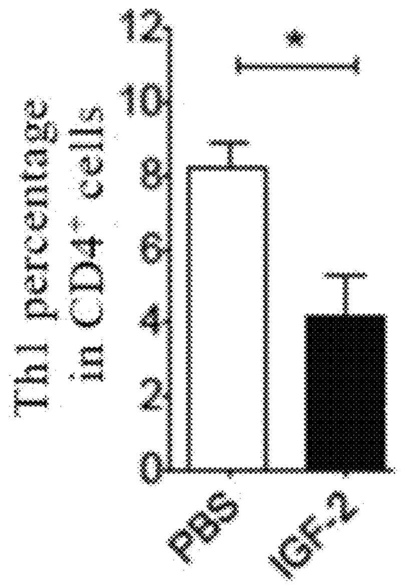
Figure 1F:
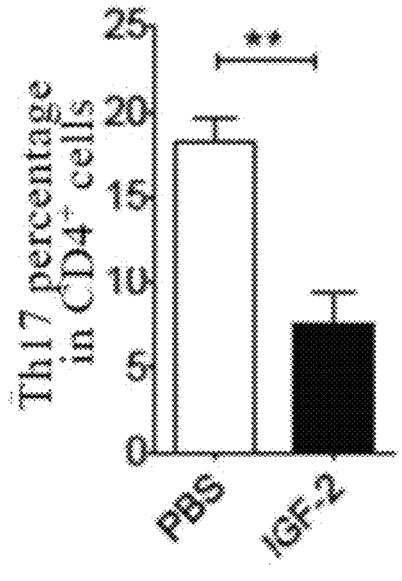
Figure 1G:
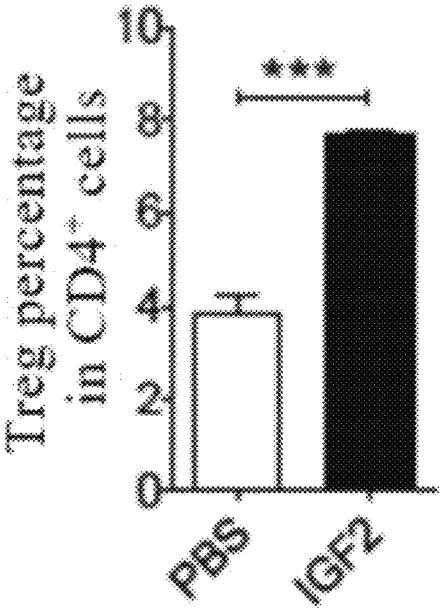
Figure 1H:
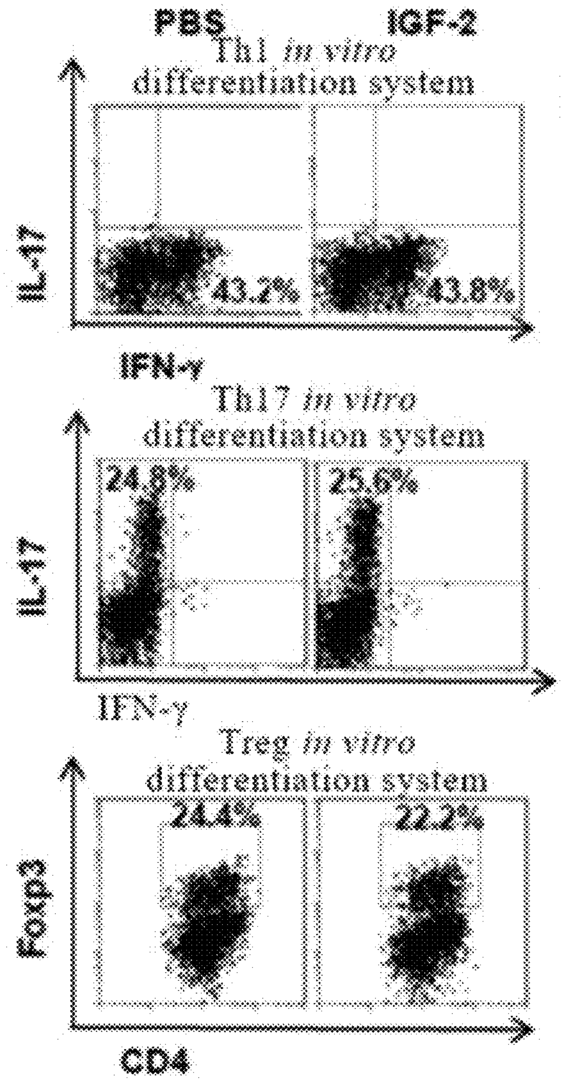

$IGF_{25-91}$ can Treat Experimental Autoimmune Encephalomyelitis (EAE) Depending on its Regulation of Gene Expression in Macrophages When treated with $IGF_{25-91}$ in mice induced EAE, it was observed that $IGF_{25-91}$ effectively alleviated the pathogenesis and severity of EAE, which was manifested by decreased clinical score, decreased number of infiltrating mononuclear cells in the spinal cord, and decreased proliferation of MOG-specific T cells in EAE mice (FIGS. 1*a-c*). Meanwhile, flow cytometry analysis showed that the use of $IGF_{25-91}$ could effectively reduce the proportions of Th1 and Th17 in the spinal cord of EAE mice and increase the proportion of Treg (FIGS. 1*d-g*). However, when the inventor added $IGF_{25-91}$ directly into an in vitro differentiation system of T cells, it was found that the differentiation efficiency of T cells into Th1, Th17 and Treg was not affected, suggesting that $IGF_{25-91}$ had an indirect effect on T cells (FIG. 1*h*).

Figure 1I:
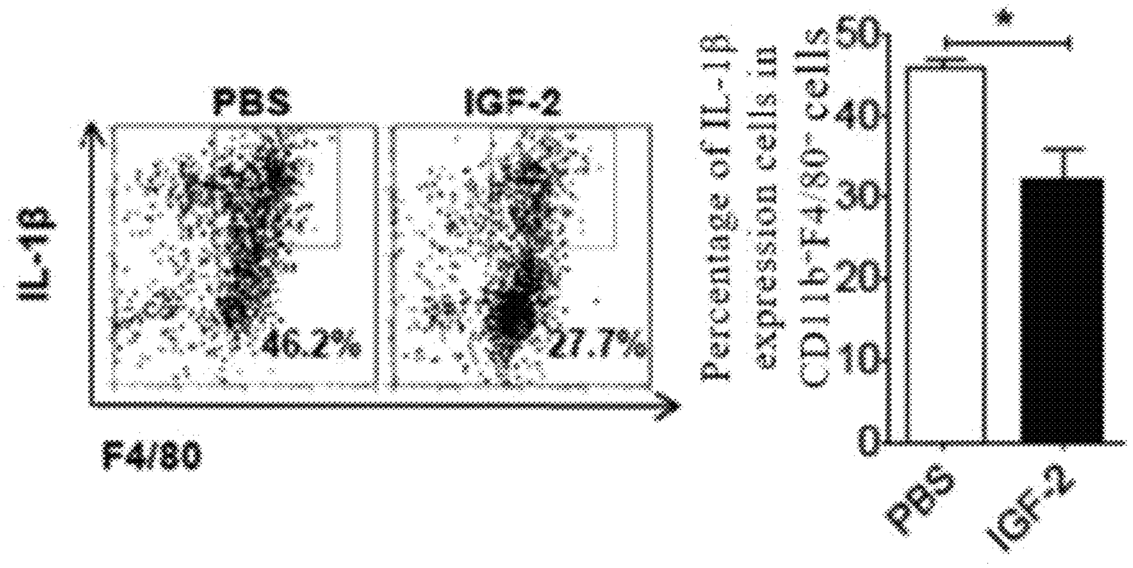
Figure 1J:
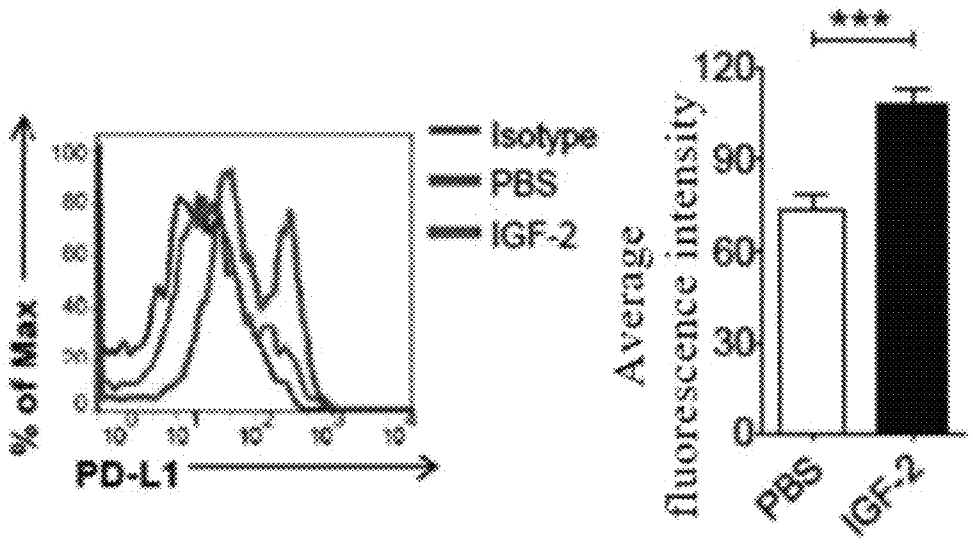
Figure 2A:
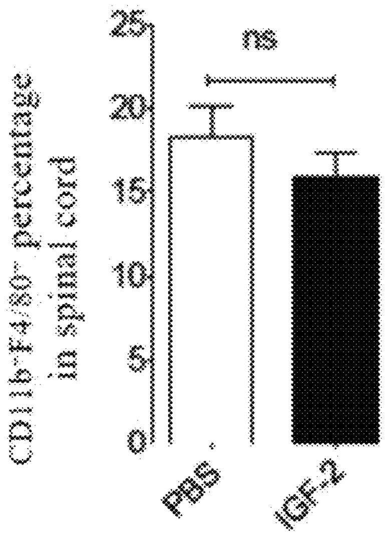
FIGS. 2A-2G show that insulin-like growth factor-2 (IGF-2) can induce anti-inflammatory macrophages.
Figure 2B:
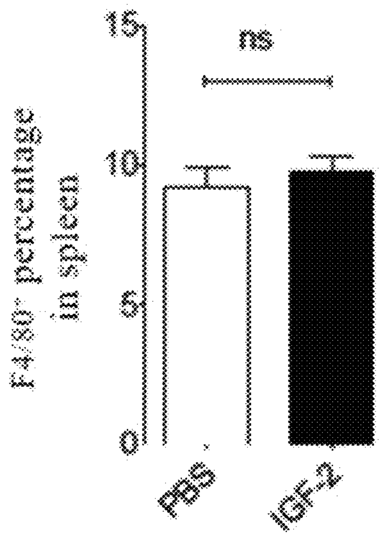
Figure 2C:
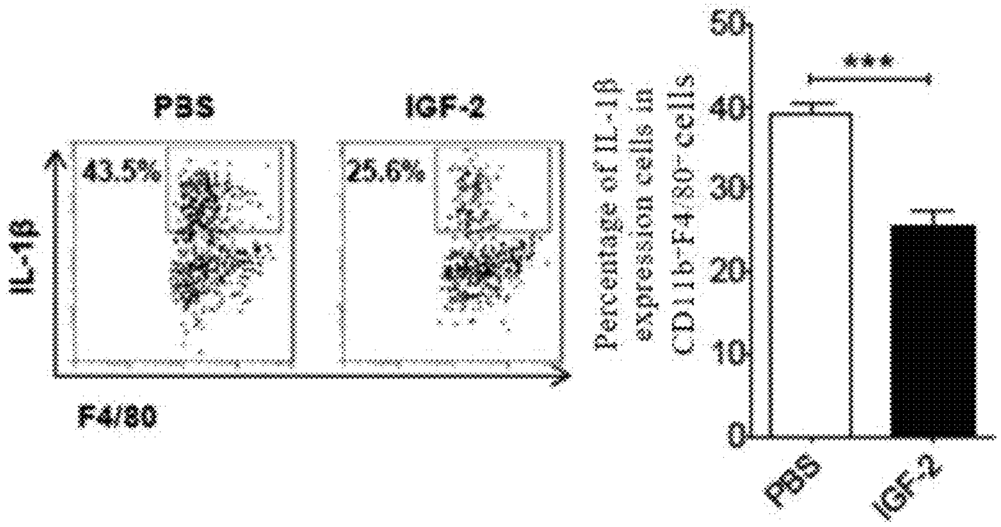
Figure 2D:
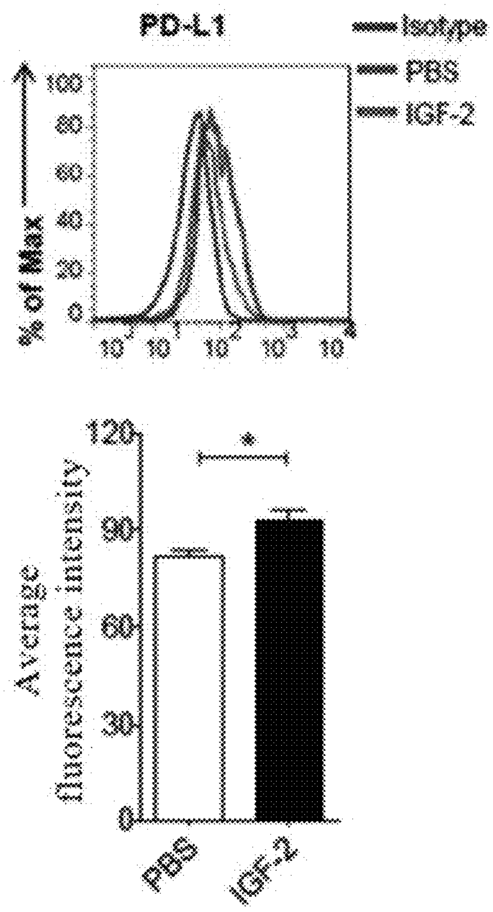
Figure 2E:
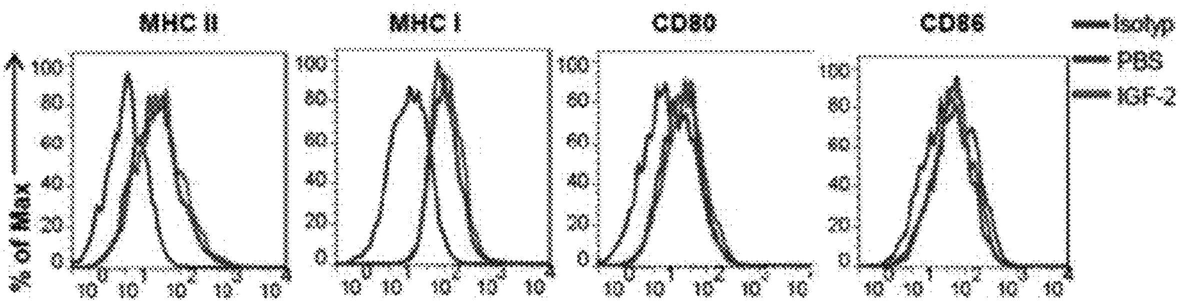
Figure 2F:
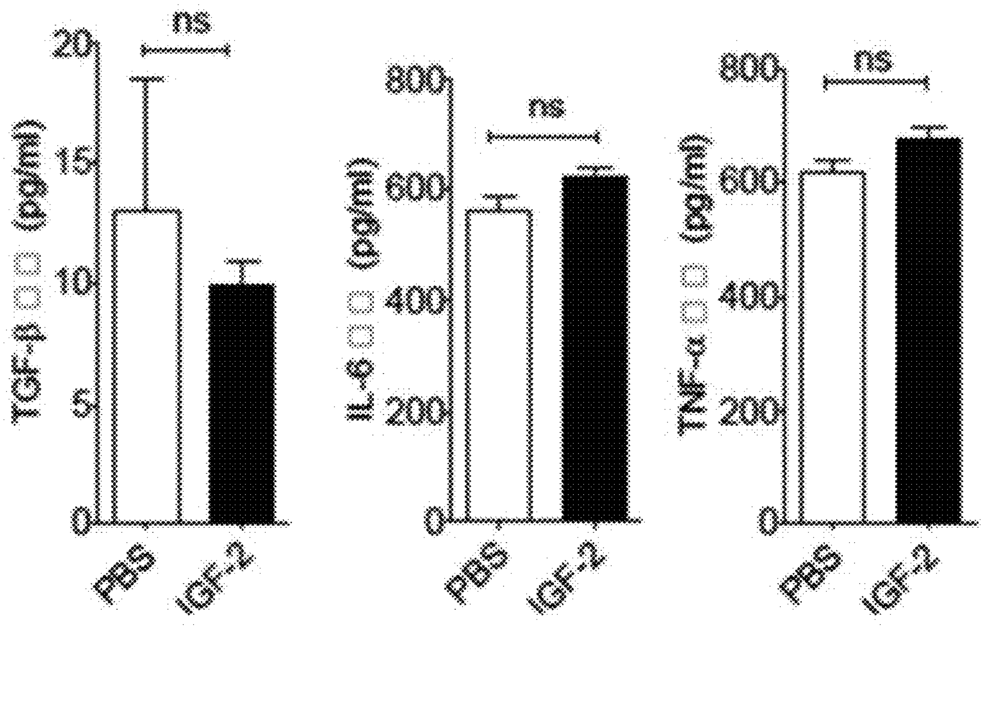
Figure 2G:
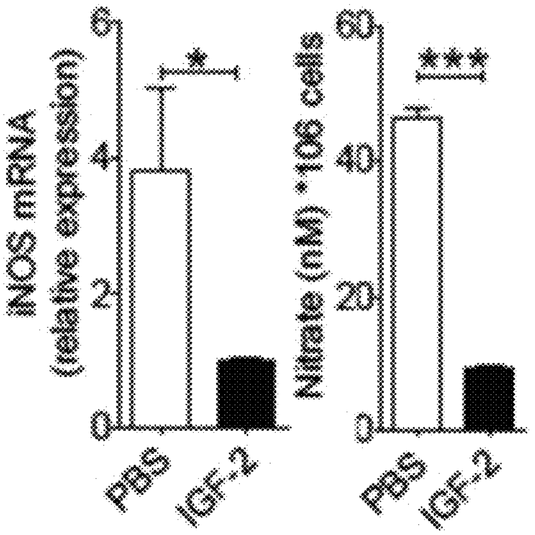

When flow cytometry instrument was used to analyze immune cells in EAE mice, it was also found that although the use of $IGF_{25-91}$ did not affect the percentage of macrophages in the spinal cord and spleen in EAE disease mice (FIGS. 2*a-b*), it could significantly affect the gene expression in macrophages, which was shown as significantly decreased expression of IL-1β and significantly increased expression of PD-L1 in macrophages (FIGS. 1*i-j*; FIGS. 2*c-d*). In conclusion, $IGF_{25-91}$ can be used in the treatment of EAE and can influence the ratio of different T cell subsets and the gene expression of macrophages in diseased mice.

Example 2

Figure 3A:
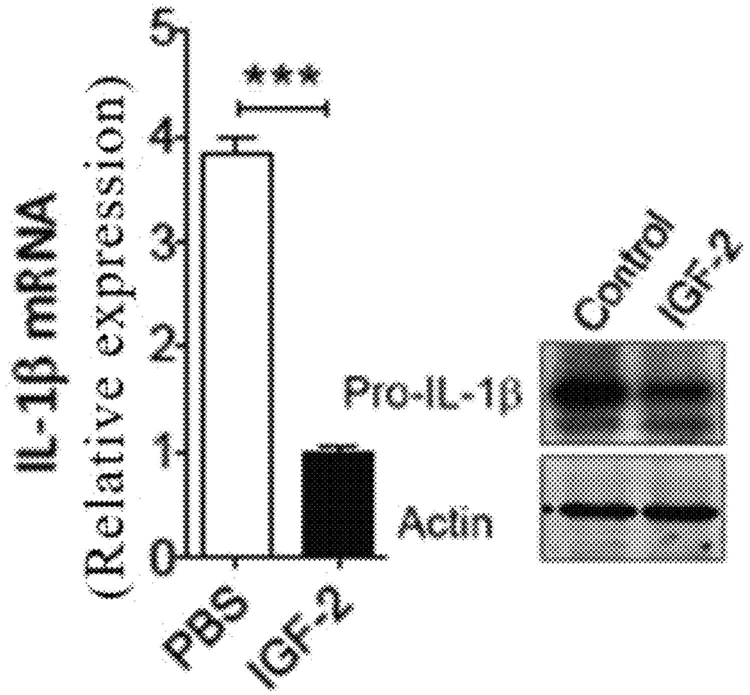
FIGS. 3A-3G show that insulin-like growth factor-2 (IGF-2) treated macrophages are effective in treating EAE.
Figure 3B:
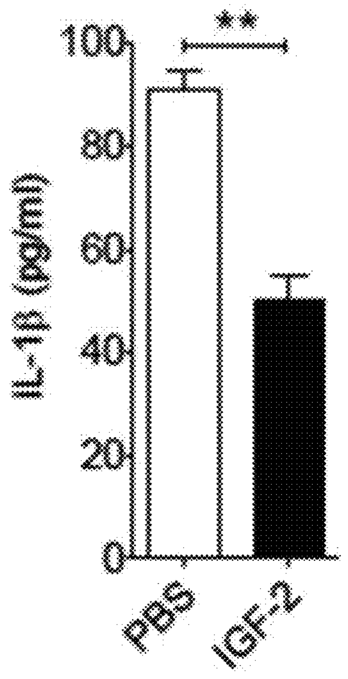
Figure 3C:
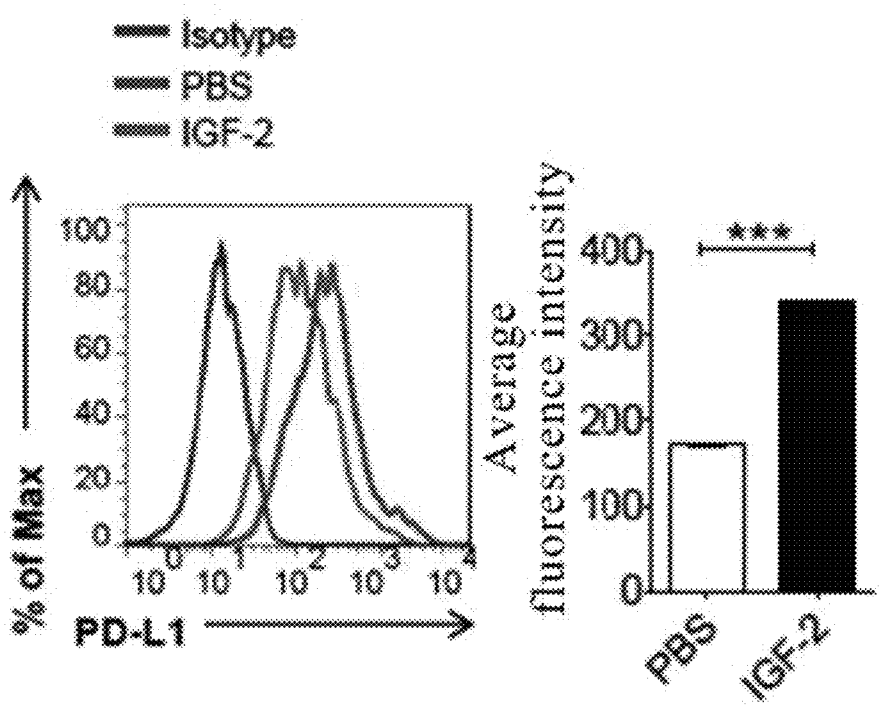
Figure 3D:
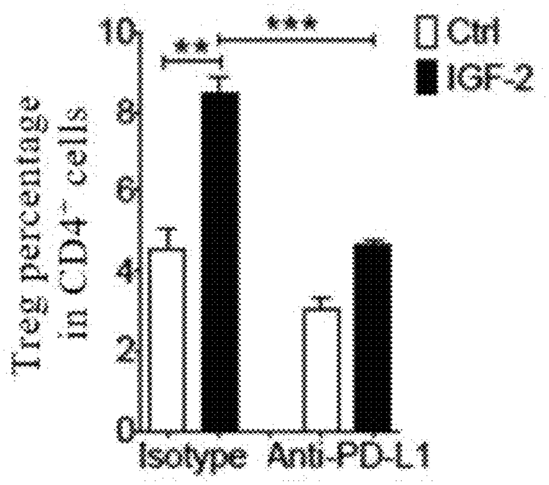
Figure 3E:
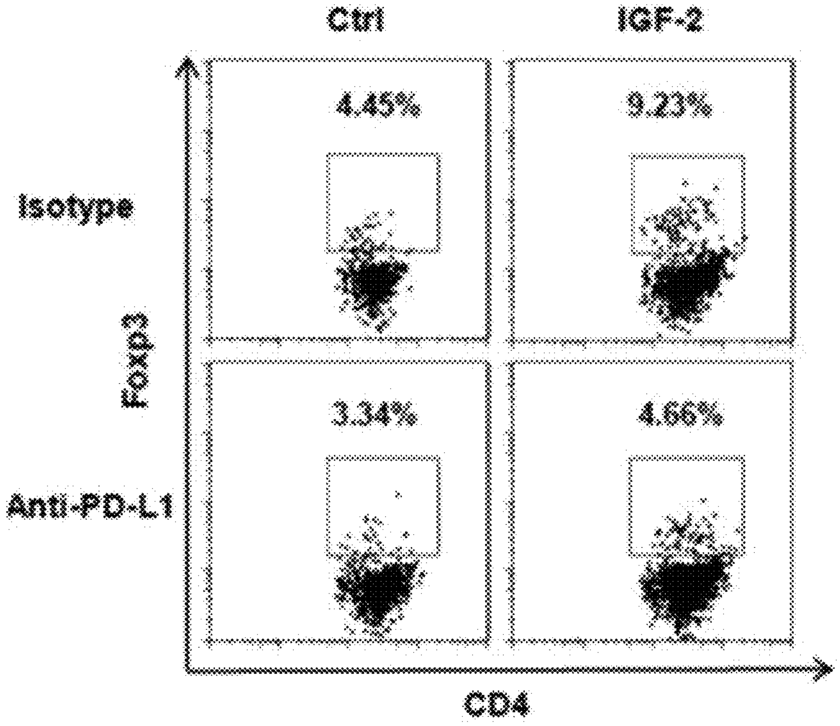
Figure 3F:
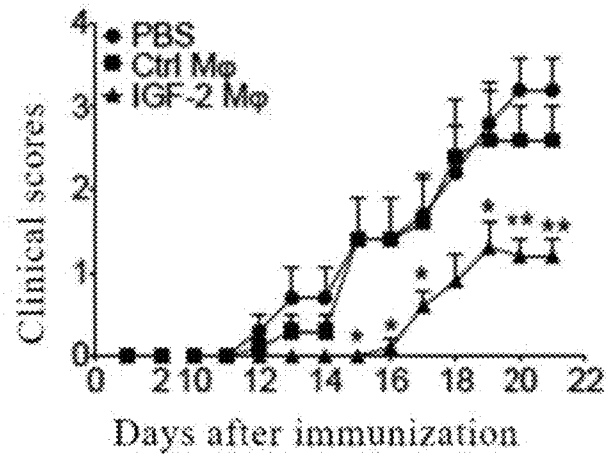
Figure 3G:
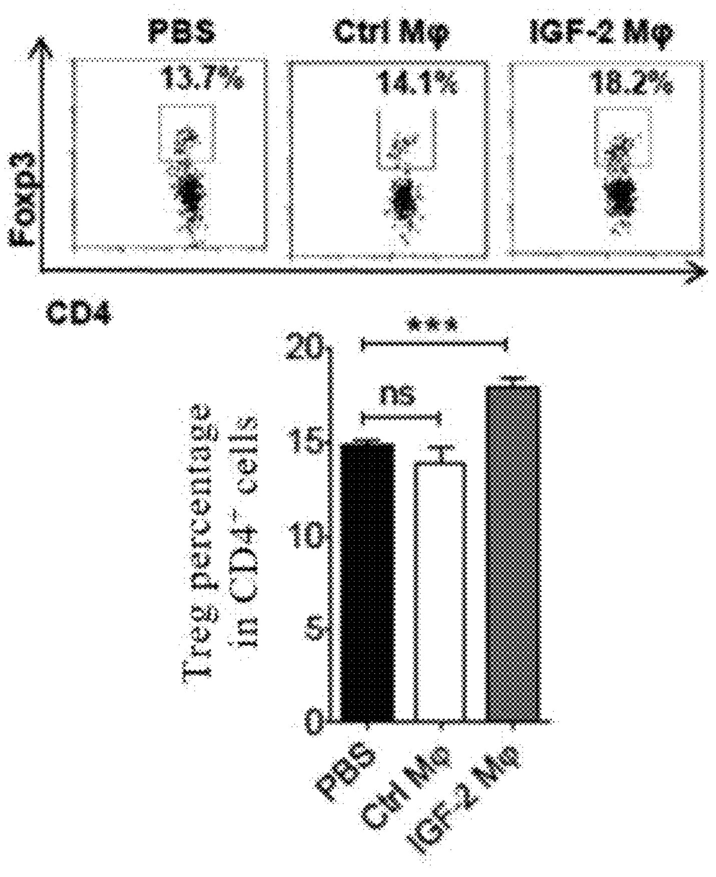
Figure 4A:
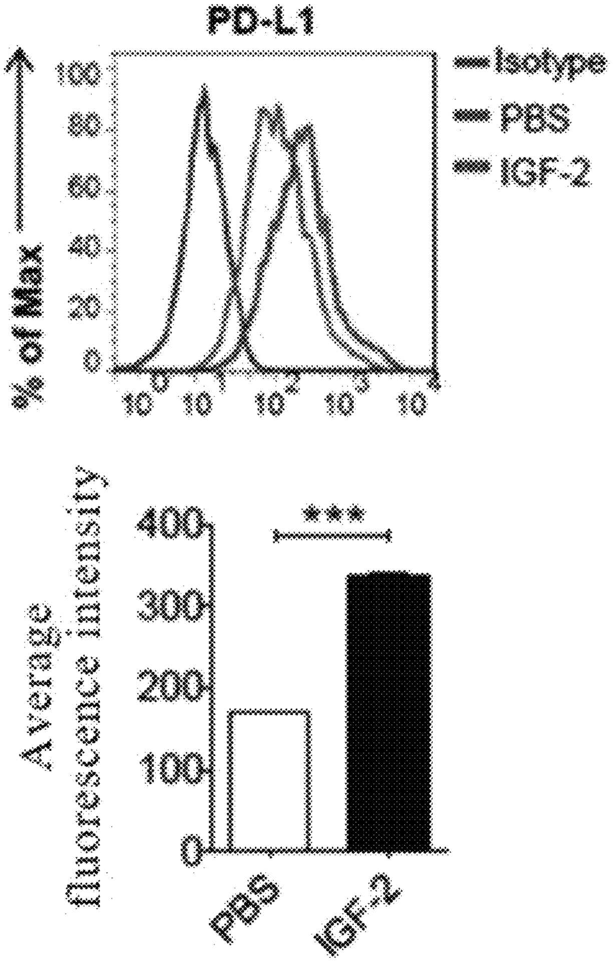
FIGS. 4A-4D show that bone marrow derived macrophages treated with insulin-like growth factor-2 (IGF-2) to promote the differentiation ability of regulatory T cell.
Figure 4B:
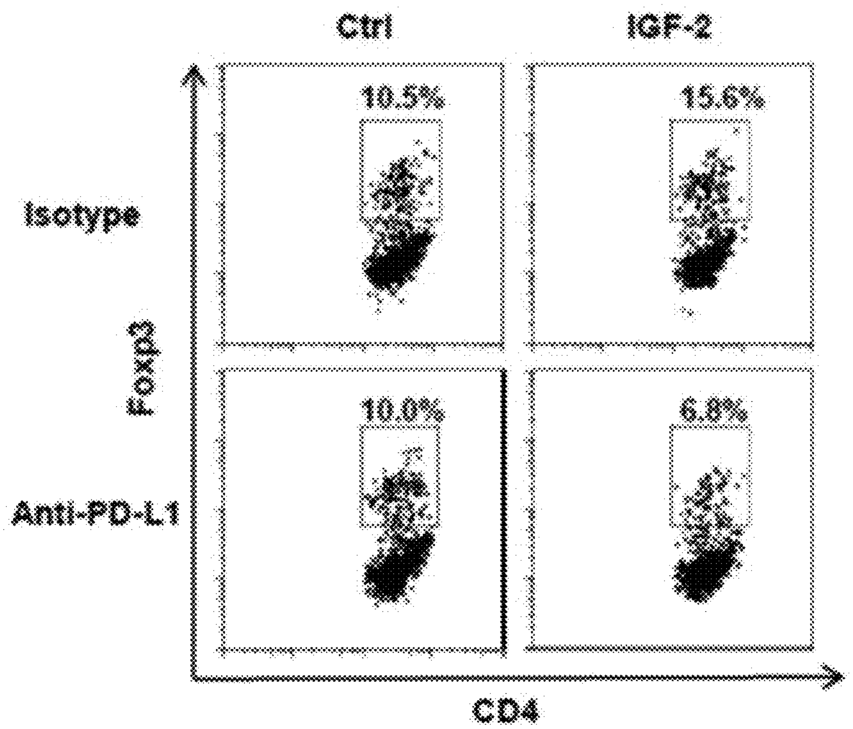
Figure 4C:
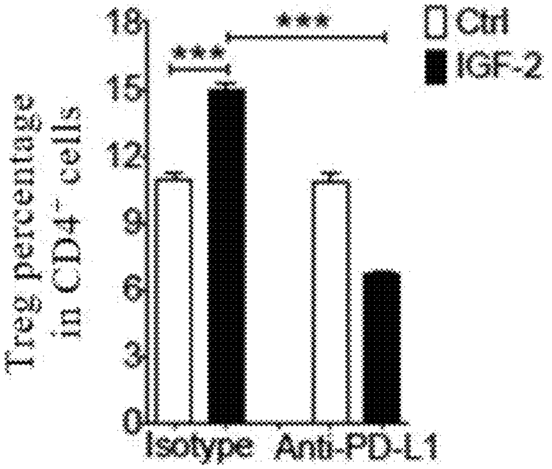
Figure 4D:
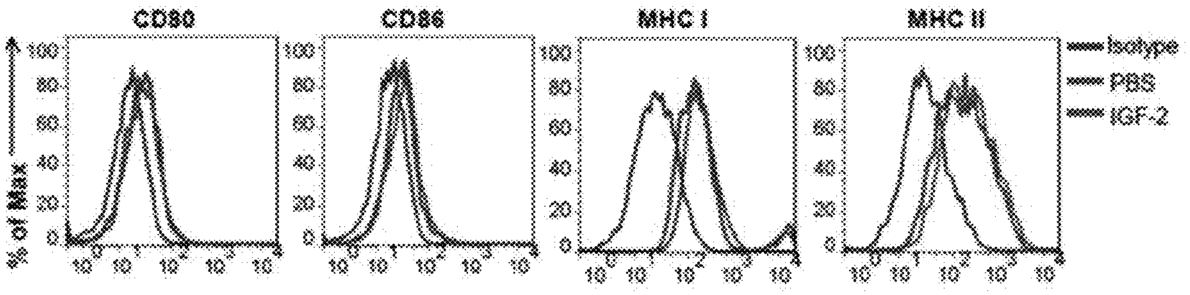

Macrophages treated with $IGF_{25-91}$ can promote the production of Treg and treat EAE In order to further study the effect of $IGF_{25-91}$ on macrophages, two classical methods were used to prepare macrophages for research. One was inducing peritoneal macrophages with thioglycollate, and the other was differentiating macrophages using bone marrow cells stimulated by L929 cell culture supernatant. It was found that after receiving $IGF_{25-91}$ treatment during the differentiation of macrophages, there was no significant change in the expression of co-stimulating molecules (CD80, CD86, MHC I, MHC II), TNF-α, IL-6, and TGF-β in peritoneal macrophages or bone marrow derived macrophages (FIG. 2*e-f*; FIG. 4*d*). However, after lipopolysaccharide stimulation, compared with control macrophages, the expression of IL-1β was significantly decreased, while the expression of PD-L1 was significantly increased in insulin-like growth factor-2 treated macrophages, which was quite consistent with the observed phenomenon in vivo (FIGS. 3*a-c*). In order to study the effect of macrophages treated with $IGF_{25-91}$ on Treg differentiation, macrophages and T cells were co-cultured, and anti-CD3, anti-CD28 and TGF-β required for Treg differentiation were added into the culture system. The results showed that, compared with normal macrophages, macrophages treated with $IGF_{25-91}$ (including bone marrow derived macrophages and peritoneal derived macrophages) could promote Treg production more effectively after LPS pre-stimulation. At the same time, PD-L1 played a crucial role in this process, because once a neutralizing antibody against PD-L1 was used, the Treg-promoting capacity of macrophages treated with $IGF_{25-91}$ was inhibited (FIGS. 3*d-e*; FIGS. 4*a-c*).

Figure 5A:
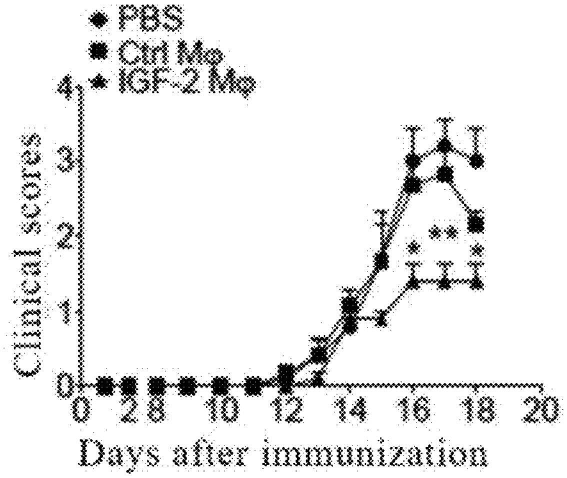
FIGS. 5A-5G show that bone marrow derived macrophages treated with insulin-like growth factor-2 (IGF-2) are effectively in alleviating experimental autoimmune encephalomyelitis (EAE) and inflammatory bowel disease (IBD).
Figure 5B:
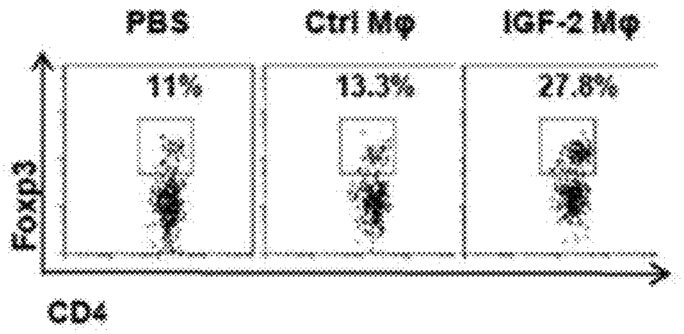
Figure 5C:
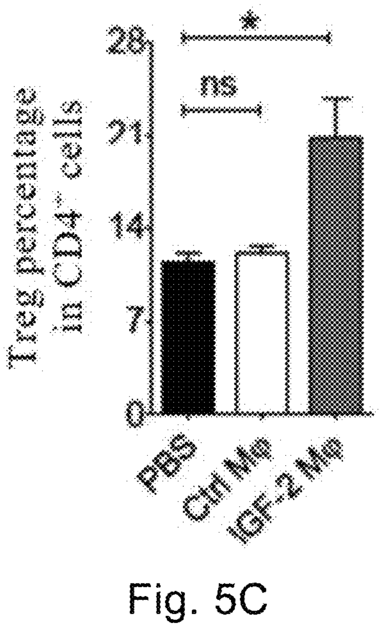
Figure 5D:
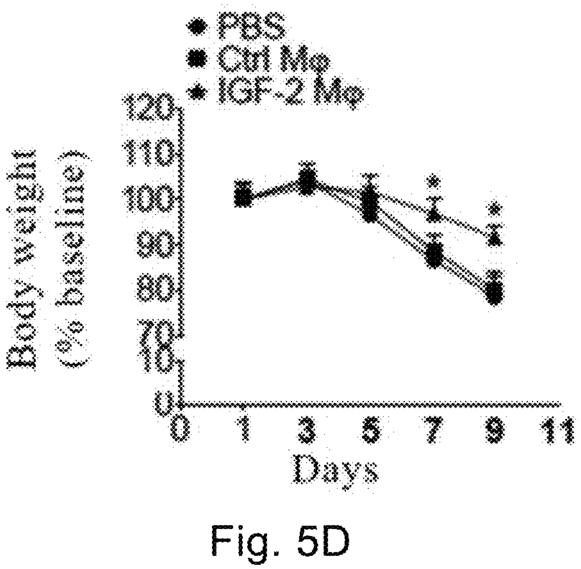
Figure 5E:
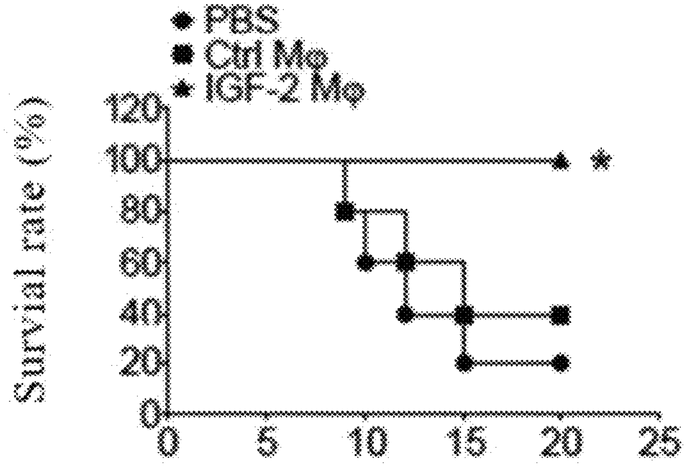
Figure 5F:
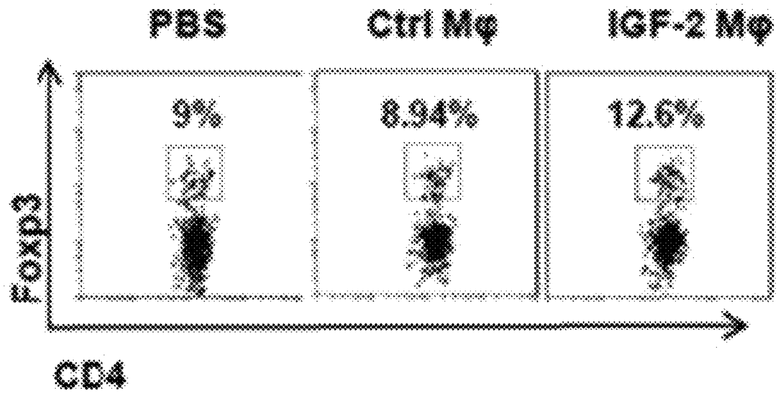
Figure 5G:
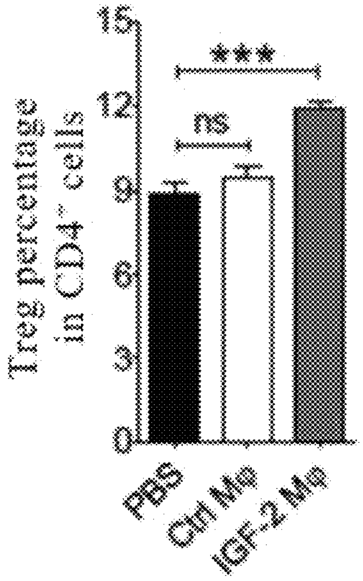

In order to further validate the immune regulation ability of macrophages treated with $IGF_{25-91}$, the treated macrophages (including bone marrow derived macrophages and peritoneal derived macrophages) were used in the treatment of EAE. The results showed that macrophages pretreated with $IGF_{25-91}$ could effectively alleviate the clinical scores of EAE, and promote the proportion of Treg in the spleen of EAE mice (FIGS. 3*f-g*; FIGS. 5*a-c*).

Example 3

Figure 6A:
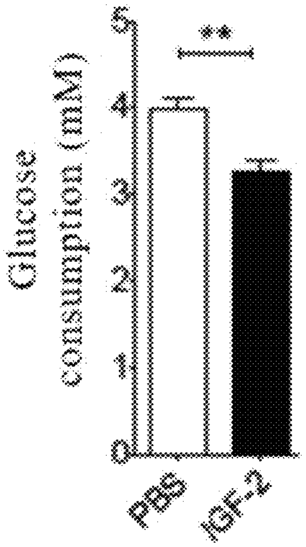
FIGS. 6A-6H show that insulin-like factor-2 (IGF-2) affects the anti-inflammatory prosperities of macrophages through regulating their glycometabolism.
Figure 6B:
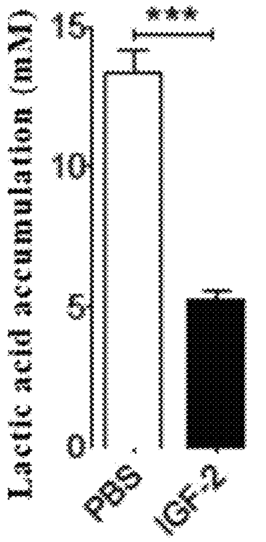
Figure 6C:
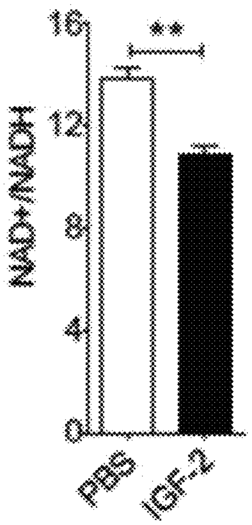
Figure 6D:
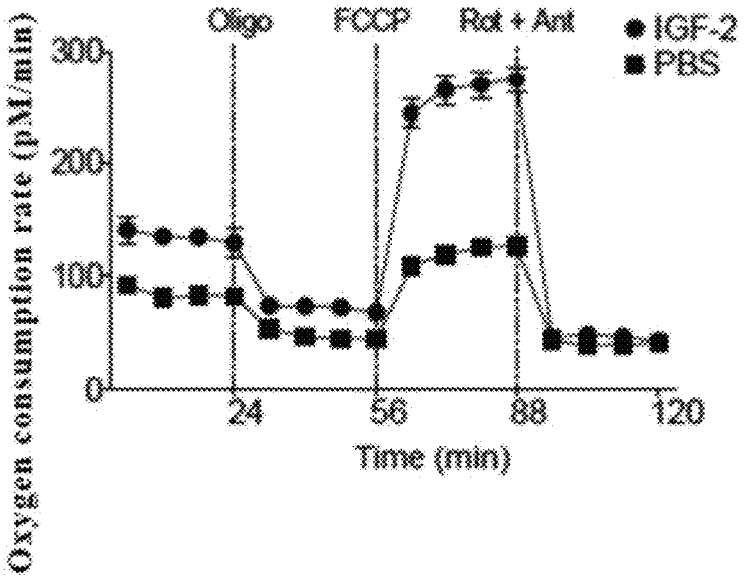
Figure 6E:
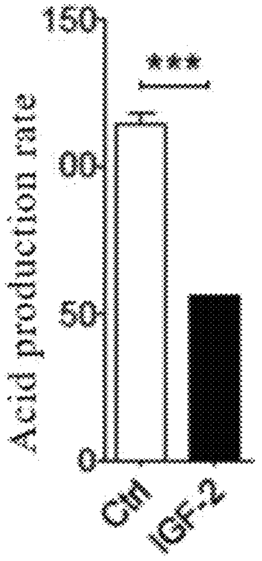
Figure 6F:
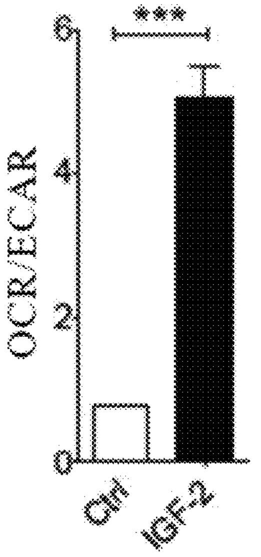

$IGF_{25-91}$ Affected Gene Expression of Macrophages Through Elevating Oxidative Phosphorylation Metabolic Pathway To investigate the regulatory mechanism of $IGF_{25-91}$ on macrophages, the properties of $IGF_{25-91}$ pre-treated macrophages and control macrophages were compared and it was found that both glucose consumption and lactate accumulation were decreased in $IGF_{25-91}$ pre-treated macrophages (FIGS. 6*a-b*). NAD+/NADH ratio in macrophages was also reduced after $IGF_{25-91}$ treatment (FIG. 6*c*), suggesting that $IGF_{25-91}$ could regulate the metabolic pathways of glycolysis and oxidative phosphorylation in macrophages. When tracking the oxygen consumption and acid production in macrophages, it was found that $IGF_{25-91}$ could effectively improve the efficiency of the oxygen consumption in macrophages, and at the same time reduce the acid production in macrophages in the background state (FIG. 6*d-f*).This suggests that $IGF_{25-91}$ can tilt macrophage metabolism toward the oxidative phosphorylation pathway.

Figure 6G:
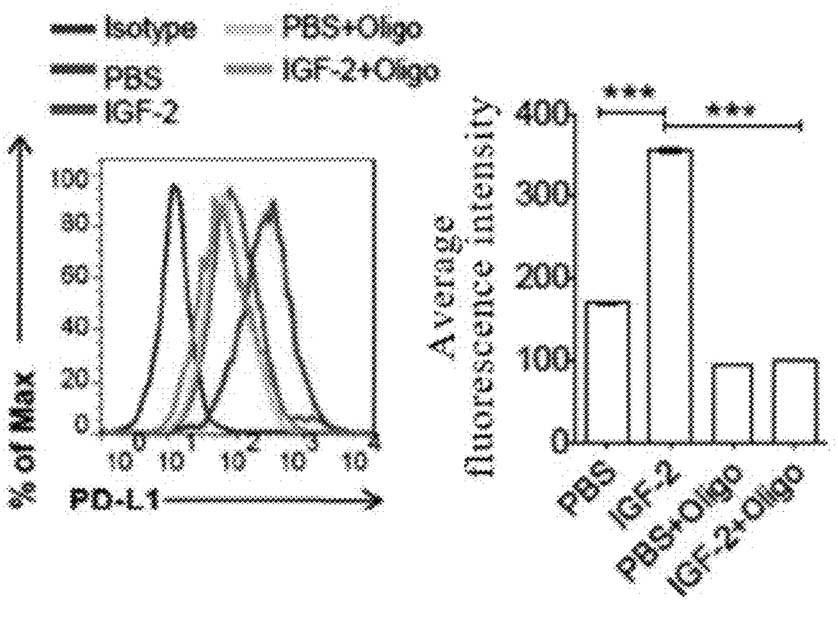
Figure 6H:
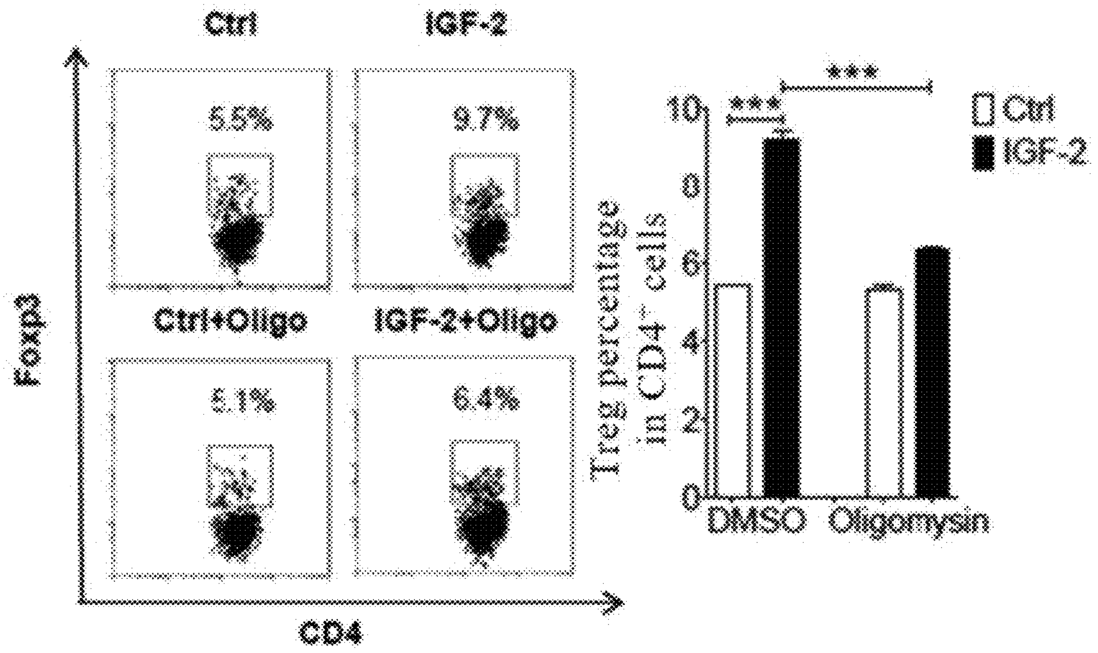

In order to confirm that the metabolic state of oxidative phosphorylation was the basis for the high expression of PD-L1 in macrophages and the promotion of Treg differentiation, oligomycin (an inhibitor of oxidative phosphorylation process) was used. It was found that once the oxidative phosphorylation was blocked, the high expression of PD-L1 in macrophages and the ability to promote the differentiation of Treg caused by $IGF_{25-91}$ disappeared (FIG. 6*g-h*). This suggests that the high expression of PD-L1 in macrophages and the ability to promote the differentiation of Treg induced by $IGF_{25-91}$ depend on the metabolic mode of oxidative phosphorylation.

Example 4

$IGF_{25-91}$ and $IGF_{25-91}$ pre-treated macrophages are effective in treating inflammatory bowel diseases (IBD).

Figure 7A:
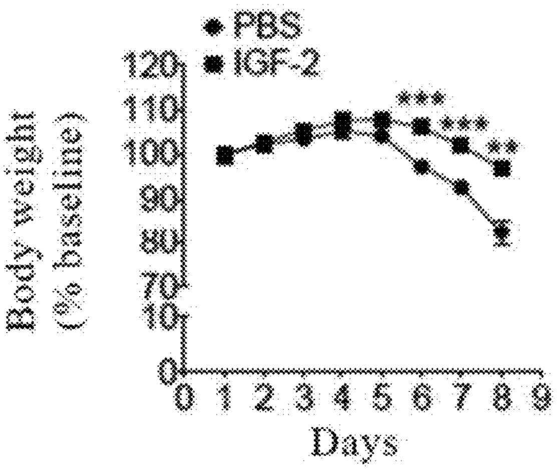
FIGS. 7A-7J show that insulin-like growth factor-2 (IGF-2) and IGF-2 treated macrophages are effective in treating experimental bowel disease.
Figure 7B:
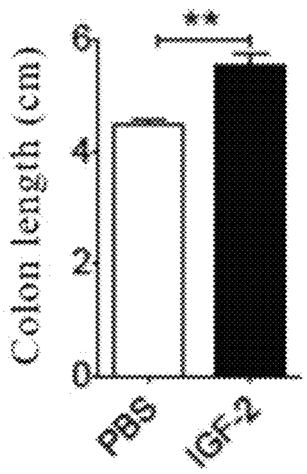
Figure 7C:
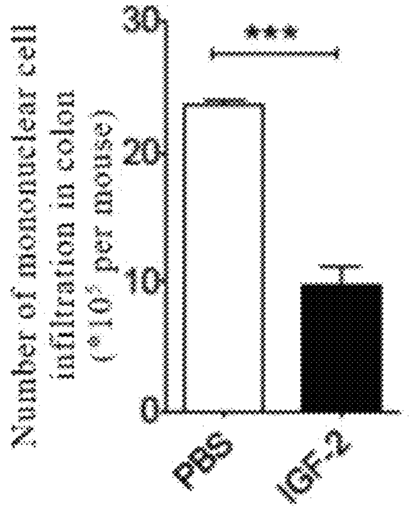
Figure 7D:
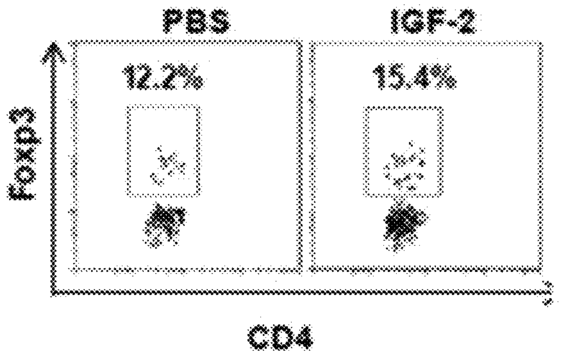
Figure 7E:
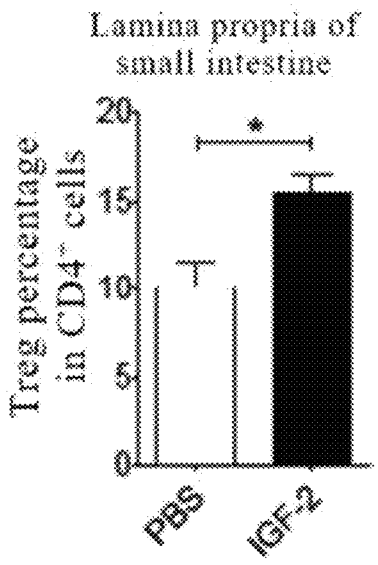
Figure 7F:
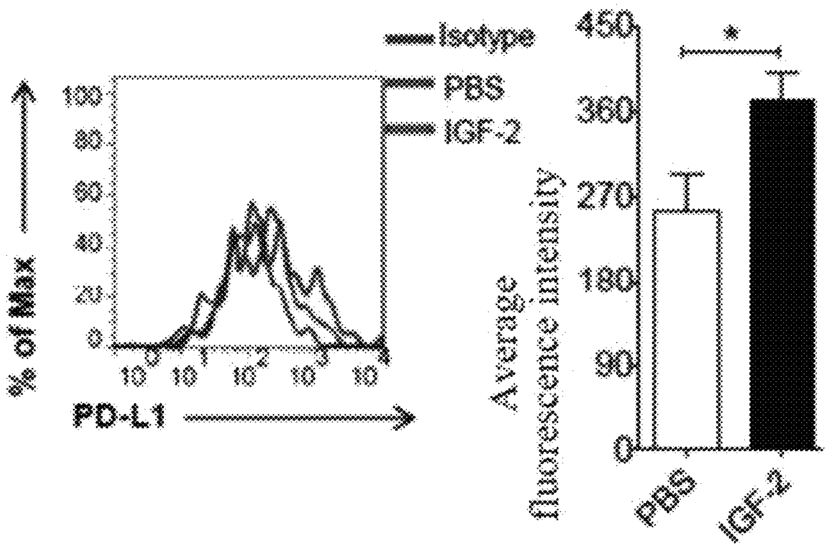
Figure 7G:
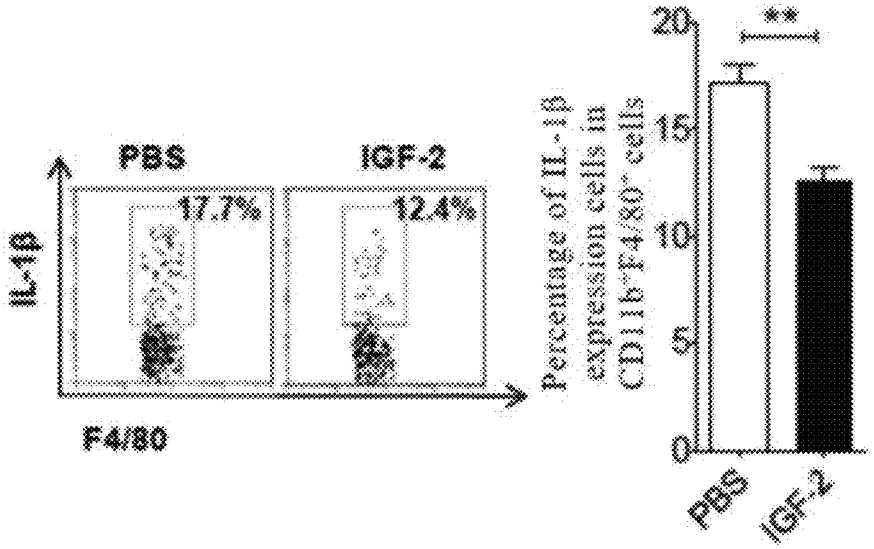
Figure 7H:
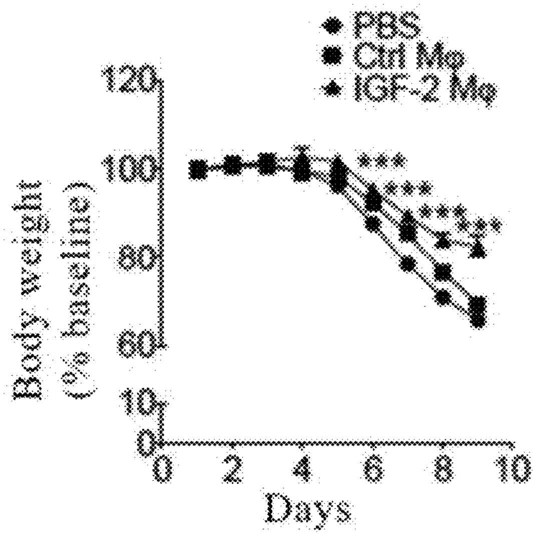
Figure 7I:
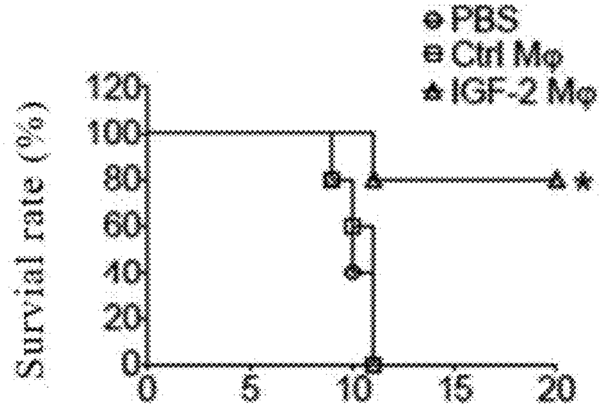
Figure 7J:
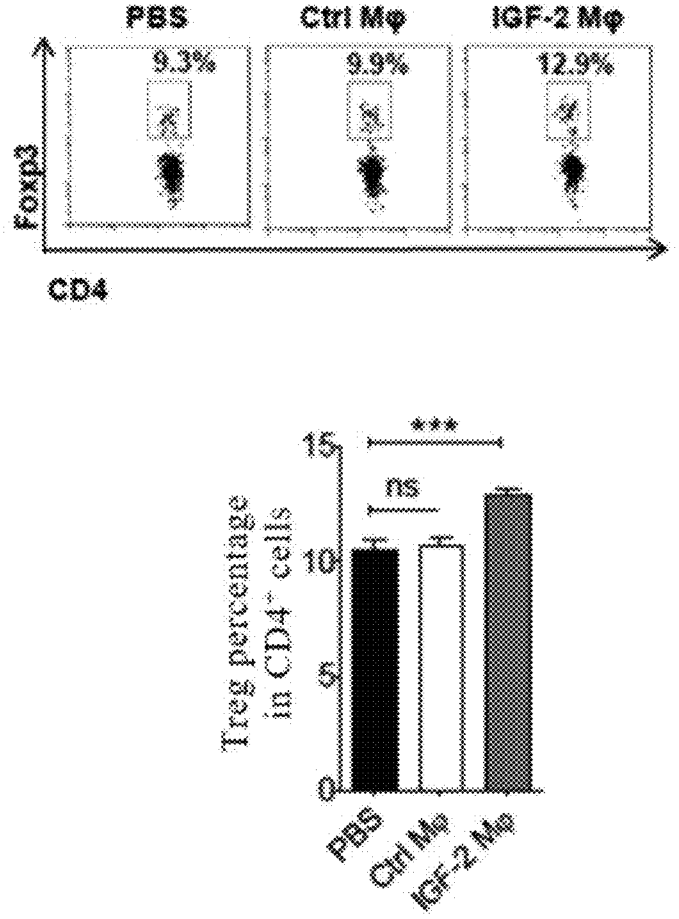
Figure 8A:
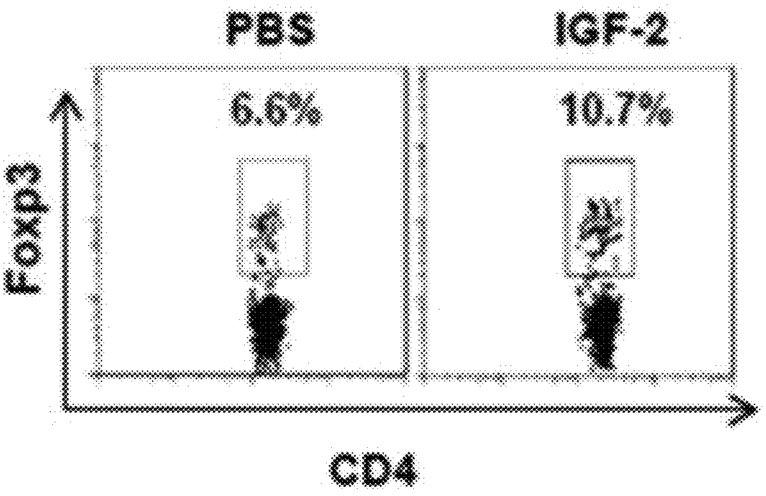
FIGS. 8A-8F show that insulin-like growth factor-2 (IGF-2) regulates immune response in the spleen and peritoneal lymph nodes of inflammatory bowel disease (IBD) mice.
Figure 8B:
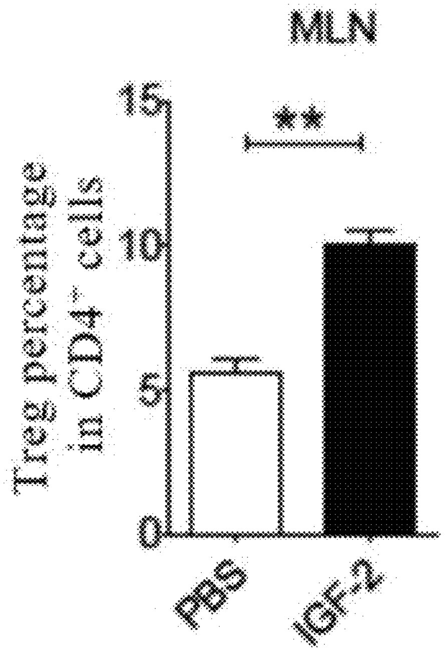
Figure 8C:
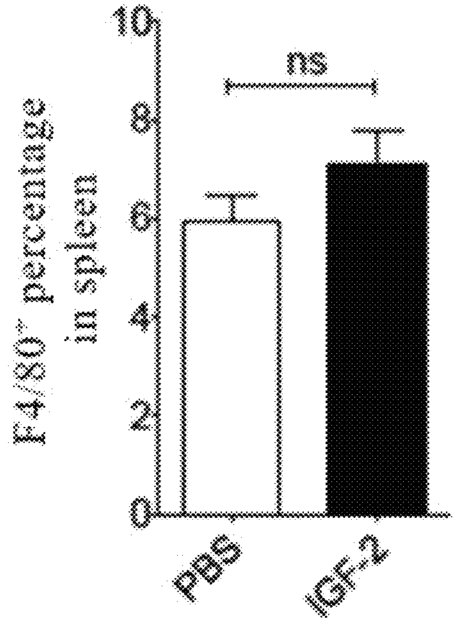
Figure 8D:
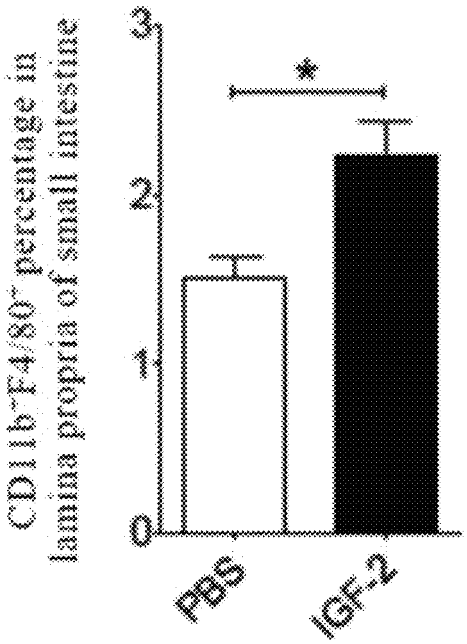
Figure 8E:
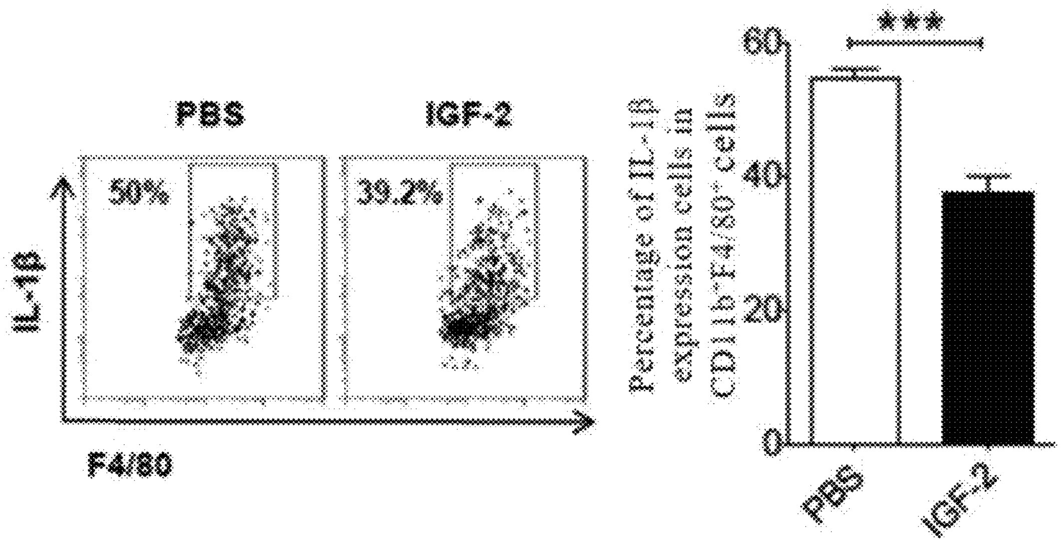
Figure 8F:
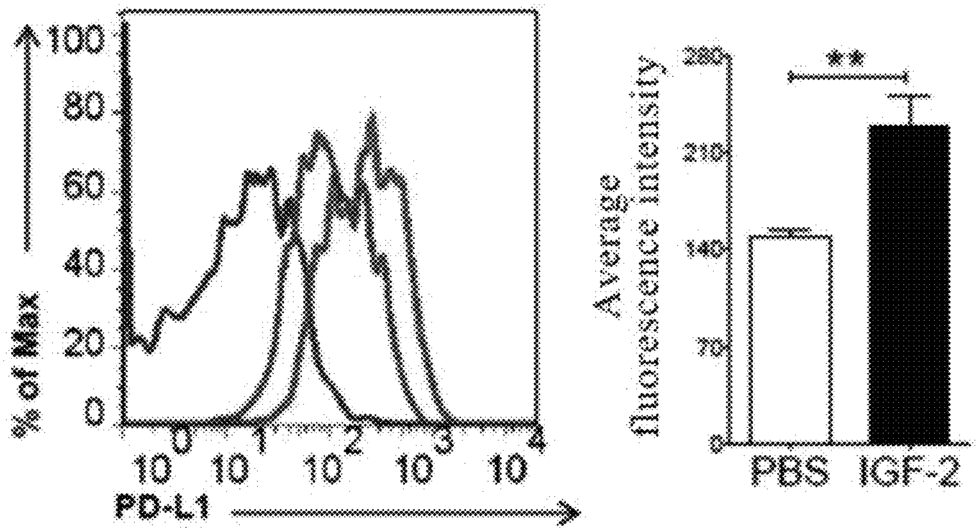
Figure 9A:
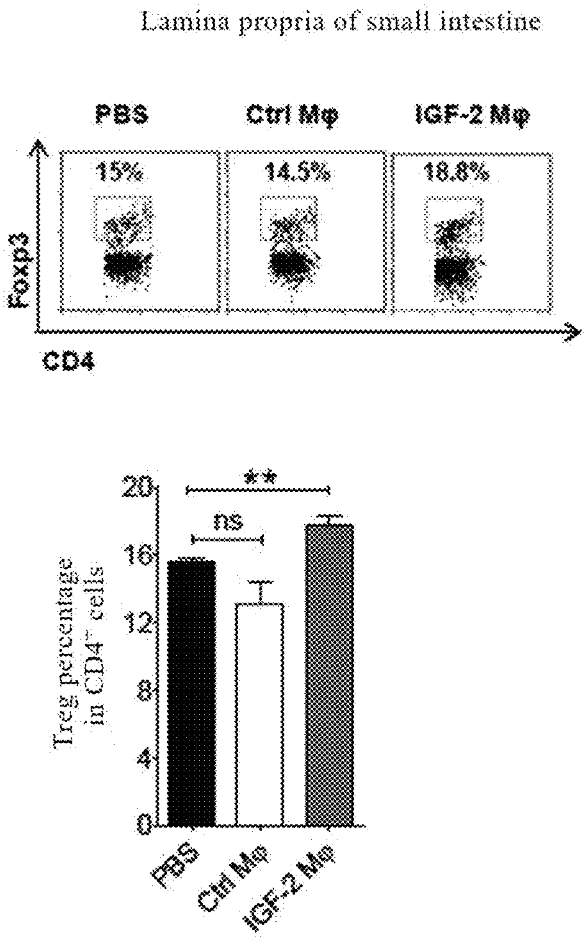
FIGS. 9A-9B show that peritoneal macrophages treated with insulin-like growth factor-2 (IGF-2) and induced by thioglycollate medium can upregulate Tregs in lamina propria of colon and peritoneal lymph nodes of IBD mice.
Figure 9B:
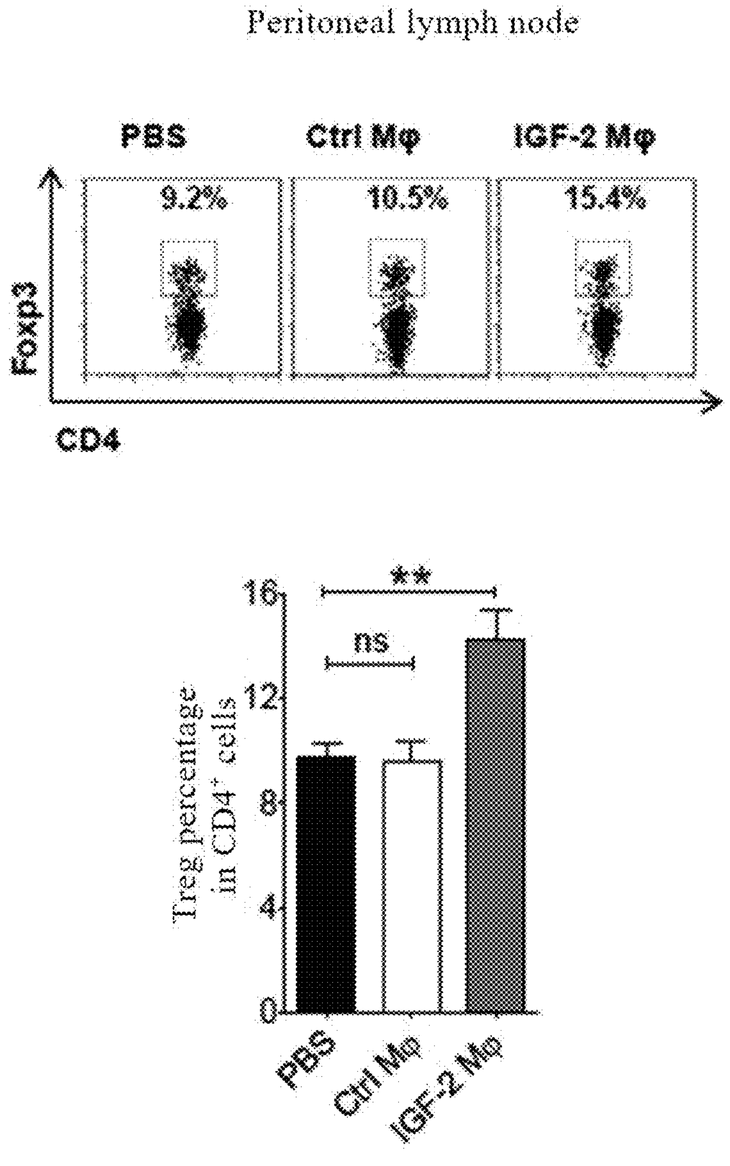

To further validate the therapeutic effects of $IGF_{25-91}$ on autoimmune diseases and the regulation of macrophages, $IGF_{25-91}$ was used to treat IBD, an autoimmune disease dominated by the innate immune system. After treatment with $IGF_{25-91}$, the weight loss of IBD mice was alleviated, colon injury and infiltration of monocytes in the colon were significantly reduced (FIGS. 7*a-c*). Flow cytometry was used to analyze T cell populations and macrophage gene expression, and it was found that $IGF_{25-91}$ could increase Treg percentages in the colon and mesenteric lymph nodes (FIGS. 7*d-e*; FIGS. 8*a-b*). Meanwhile, the decreased expression of IL-1β and the increased expression of PD-L1 in macrophages were observed in the colon and spleen (FIGS. 7*f-g*; FIGS. 8*c-f*). Moreover, $IGF_{25-91}$ pre-treated macrophages could be administered directly in the treatment of IBD to alleviate body weight loss and improve the survival rate of IBD mice (FIGS. 5*d-e*; FIGS. 7*h-i*). $IGF_{25-91}$ pre-treated macrophages also increase Treg percentages in the spleen, peyer's patches and mesenteric lymph nodes (FIGS. 5*f-g*; FIGS. 7*h-j*).

Example 5

Figure 10:
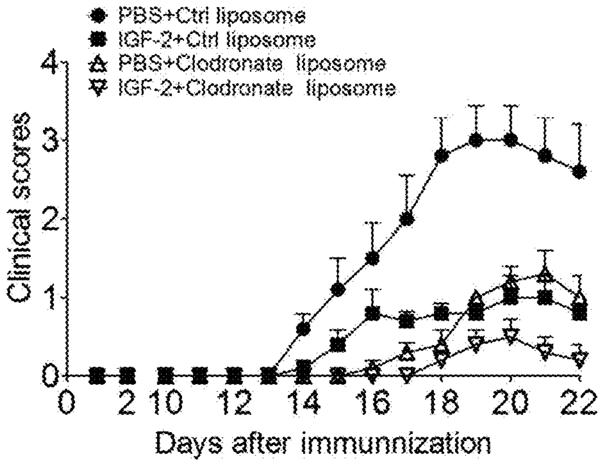
FIG. 10 shows that separate injection of insulin-like growth factor-2 (IGF-2) and clodronate liposome can significantly inhibit the progress of EAE and play an effective therapeutic role when compared with that of control mice group. Importantly, combined injection of IGF-2 and clodronate liposome has significantly better therapeutic effects on EAE than other groups.

$IGF_{25-91}$ and Macrophage Scavenger are More Effective in Treating Inflammatory Diseases $IGF_{25-91}$ can significantly inhibit inflammatory diseases, such as the above-mentioned multiple sclerosis and inflammatory bowel diseases. Moreover, this effect is closely related to the $IGF_{25-91}$ regulation on macrophages which are reprogrammed into macrophages with immunosuppressive function, thus inhibiting over-strong inflammatory response. However, when inflammatory disease occurs, systemic and local inflammation is often accompanied by a large amount of proinflammatory macrophage infiltration, and the macrophage infiltration in inflammatory site often depends on an influx of peripheral monocytes and its evolution into proinflammatory macrophages. Therefore, we investigated whether a combination of clearance of resident proinflammatory macrophages and the reprogramming function of $IGF_{25-91}$ on macrophages can optimize the treatment of inflammatory disease. On the 9th, 11th, and 13th day of EAE induction, mice in different experimental groups received $IGF_{25-91}$, Clodronate liposome (for removing macrophage) or a combined injection of $IGF_{25-91}$ and Clodronate liposome. The progress of EAE in mice was observed. It was found that single injection of $IGF_{25-91}$ and Clodronate liposome could significantly inhibit the progress of EAE and had an effective therapeutic effect compared with the control group. More importantly, a combined injection of $IGF_{25-91}$ and Clodronate liposome had a more significant therapeutic effect on EAE compared with other groups (FIG. 10). Therefore, the combination therapy of $IGF_{25-91}$ and macrophage scavenger has a more optimized effect in the treatment of inflammatory diseases by reprogramming cells into macrophages with immunosuppressive function.

Example 6

$IGF_{25-91}$ pre-treated macrophages can be used to treat obesity-induced insulin resistance.

Figure 13A:
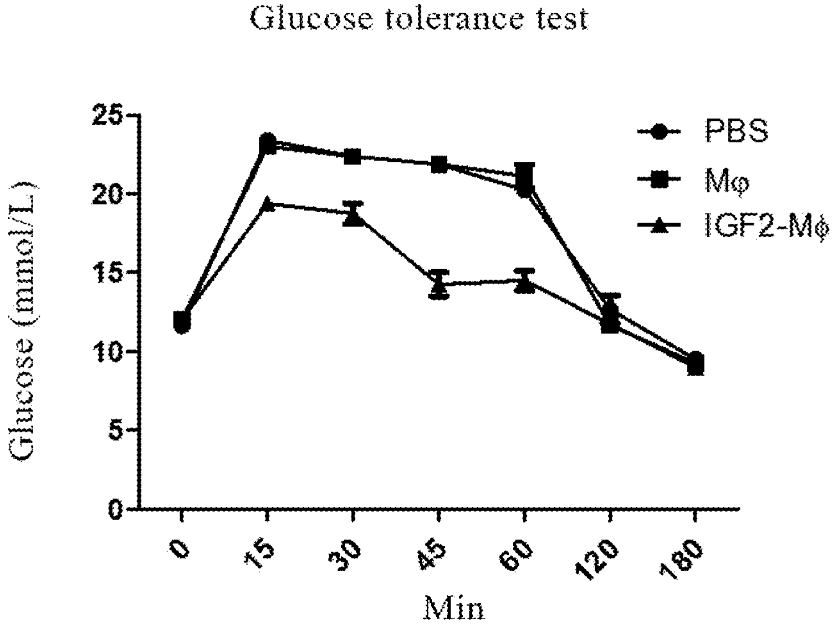
FIG. 13A shows the results of glucose tolerance test.
Figure 13B:
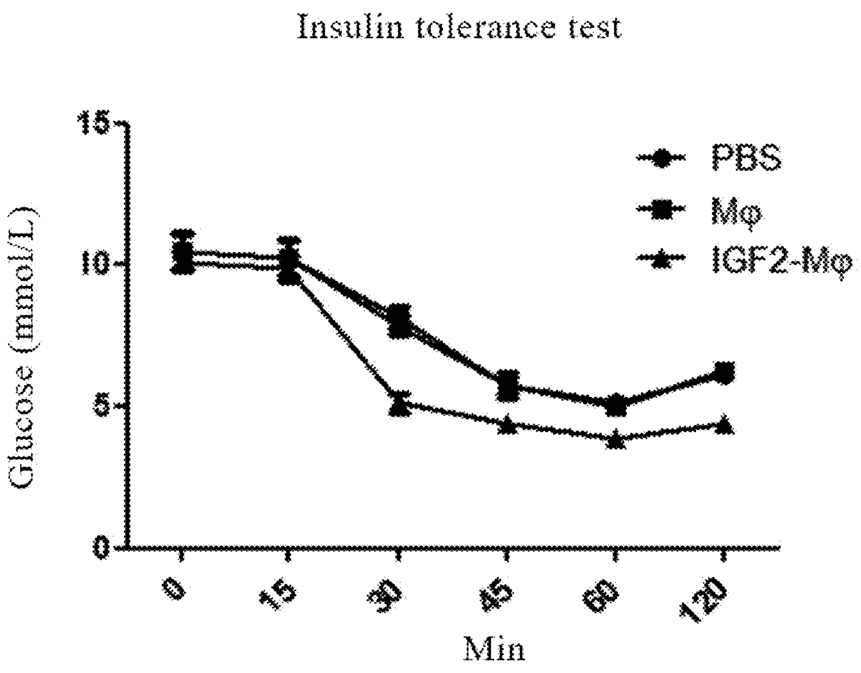
FIG. 13B shows the results of insulin tolerance test.

Mice were fed with high fat diet for 20 weeks and then injected with PBS, macrophages ($5\times10^6$) or $IGF_{25-91}$ pre-treated macrophages ($5\times10^6$). Two weeks after the treatment, glucose tolerance test and insulin tolerance test were conducted, and glucose changes in each group were detected. The results showed that $IGF_{25-91}$ pre-treated macrophages could significant improve the ability of glucose tolerance in the insulin resistance mice (FIGS. 13A and 13B). These results demonstrated that $IGF_{25-91}$ pre-treated macrophages were effective in treating insulin resistance and diabetes.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

SEQUENCE LISTING

```
Sequence total quantity: 2
SEQ ID NO: 1          moltype = AA  length = 180
FEATURE               Location/Qualifiers
source                1..180
                      mol_type = protein
                      organism = Homo sapiens
SEQUENCE: 1
MGIPMGKSML VLLTFLAFAS CCIAAYRPSE TLCGGELVDT LQFVCGDRGF YFSRPASRVS  60
RRSRGIVEEC CFRSCDLALL ETYCATPAKS ERDVSTPPTV LPDNFPRYPV GKFFQYDTWK  120
QSTQRLRRGL PALLRARRGH VLAKELEAFR EAKRHRPLIA LPTQDPAHGG APPEMASNRK  180

SEQ ID NO: 2          moltype = AA  length = 67
FEATURE               Location/Qualifiers
source                1..67
                      mol_type = protein
                      organism = Homo sapiens
SEQUENCE: 2
AYRPSETLCG GELVDTLQFV CGDRGFYFSR PASRVSRRSR GIVEECCFRS CDLALLETYC  60
ATPAKSE                                                            67
```

The invention claimed is:

1. A method of promoting differentiation of regulatory T cell; and inhibiting differentiation of Th1 cell and/or Th17 cell, comprising a step of: administering a macrophage treated with insulin-like growth factor-2 (IGF-2) or an active fragment having amino acids from position 25 to position 91 of IGF-2, to a subject; wherein the macrophage is cultured in the presence of IGF-2 or the active fragment to obtain the macrophage treated with the IGF-2 or the active fragment; and in the macrophage, the PD-L1 expression is up-regulated and/or the IL-1β expression is down-regulated.

2. The method of claim 1, wherein the macrophage is cultured in the presence of IGF-2.

3. The method of claim 1, wherein the macrophage is cultured in the presence of the active fragment, the active fragment having amino acids from position 25 to position 91 of IGF-2.

4. The method of claim 1, wherein the amino acid sequence of the IGF-2 is shown in SEQ ID NO: 1.

5. A method of treating a subject having an autoimmune disease, comprising a step of: administering a macrophage treated with insulin-like growth factor-2 (IGF-2) or an active fragment having amino acids from position 25 to position 91 of IGF-2, to the subject; wherein the macrophage is cultured in the presence of IGF-2 or the active fragment to obtain the macrophage treated with the IGF-2 or the active fragment; and in the macrophage, the PD-L1 expression is up-regulated and/or the IL-1β expression is down-regulated.

6. The method of claim 5, wherein the autoimmune disease is selected from the group consisting of multiple sclerosis, inflammatory bowel disease, autoimmune encephalomyelitis, autoimmune hepatitis, systemic lupus erythematosus, rheumatoid arthritis, insulin resistance, diabetes, liver cirrhosis, and a combination thereof.

* * * * *